(12) United States Patent
Ma et al.

(10) Patent No.: US 8,709,464 B2
(45) Date of Patent: *Apr. 29, 2014

(54) POROUS OBJECTS HAVING IMMOBILIZED ENCAPSULATED BIOMOLECULES

(75) Inventors: Peter X. Ma, Ann Arbor, MI (US); Guobao Wei, Eatontown, NJ (US); William V. Giannobile, Ann Arbor, MI (US); Qiming Jin, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1031 days.

This patent is subject to a terminal disclaimer.

(21) Appl. No.: 11/972,531

(22) Filed: Jan. 10, 2008

(65) Prior Publication Data

US 2008/0317816 A1 Dec. 25, 2008

Related U.S. Application Data

(60) Provisional application No. 60/896,107, filed on Mar. 21, 2007, provisional application No. 60/884,283, filed on Jan. 10, 2007.

(51) Int. Cl.
*A61F 2/00* (2006.01)
*A61L 31/16* (2006.01)
*A61K 38/18* (2006.01)
*A61K 38/20* (2006.01)
*A61K 38/19* (2006.01)
*A61K 9/14* (2006.01)

(52) U.S. Cl.
CPC .............. *A61L 31/16* (2013.01); *A61K 38/1833* (2013.01); *A61K 38/1875* (2013.01); *A61K 38/206* (2013.01); *A61K 38/1891* (2013.01); *A61K 38/191* (2013.01); *A61K 9/14* (2013.01)

USPC .......... 424/423; 424/85.2; 424/459; 514/8.2; 514/8.8; 514/9.5

(58) Field of Classification Search
None
See application file for complete search history.

(56) References Cited

U.S. PATENT DOCUMENTS

| 6,146,892 | A  | * | 11/2000 | Ma et al. .................... 435/399 |
| 6,582,471 | B1 | * | 6/2003  | Bittmann et al. .......... 623/23.63 |
| 2003/0219466 | A1 | * | 11/2003 | Kumta et al. ................ 424/423 |
| 2004/0105878 | A1 |   | 6/2004  | Schwendeman et al. |
| 2006/0246121 | A1 |   | 11/2006 | Ma et al. |
| 2008/0095815 | A1 | * | 4/2008  | Mao ............................. 424/422 |

OTHER PUBLICATIONS

Schier et al "Recombinant Human Bone Morphogenetic Protein-2 Binding and Incoporation in PLGA Microsphere Delivery Systems", Pharmaceutical Development and Technology, 4(4), 611-621 (1999).*
Wei, G., Q. Jin, W.V. Giannobile and P.X. Ma, "The enhancement of osteogenesis by nano-fibrous scaffolds incorporating rhBMP-7 nanospheres," Biomaterials, 2007, 28, pp. 2087-2096.
Heldin, C.H., and B. Westermark "Mechanism of action and in vivo role of platelet-derived growth factor," Physiological Reviews, 1999, 79.4, pp. 1283-1316 (20 printed pages).

(Continued)

*Primary Examiner* — Bethany Barham
(74) *Attorney, Agent, or Firm* — Dierker & Associates, P.C.

(57) ABSTRACT

A porous object includes a porous material having internal pore surfaces and external pore surfaces. Releasing material encapsulated biomolecules are immobilized on at least one of the internal pore surfaces, at least one of the external pore surfaces, or combinations thereof.

14 Claims, 16 Drawing Sheets

(56) References Cited

OTHER PUBLICATIONS

Cooke, J.W., D.P. Sarment, L.A. Whitesman, S.E. Miller, Q. Jin, et al., "Effect of rhPDGF-BB Delivery on Mediators of Periodontal Wound Repair," Tissue Eng, 2006, 12, 6, pp. 1441-1450.
Kaplan, D.R., F.C. Chao, C.D. Stiles, H.N. Antoniades and C.D. Scher, "Platelet alpha granules contain a growth factor for fibroblasts," Blood, 1979, 53, pp. 1043-1052.
Rosenkranz, S. and A. Kazlauskas, "Evidence for Distinct Signaling Properties and Biological Responses Induced by the PDGF Receptor Subtypes," Growth Factors, 1999, 16, pp. 201-216.
Seppä, H., G. Grotendorst, S. Seppä, E. Schiffmann and G.R. Martin, "Platelet-derived Growth Factor in Chemotactic for Fibroblasts," Journal of Cell Biology, 1982, 92, pp. 584-588.
Hsieh, P.C., M.E. Davis, J. Gannon, C. MacGillivray and R.T. Lee, "Controlled delivery of PDGF-BB for myocardial protection using injectable self-assembling peptide nanofibers," Journal of Clinical Investigation, 2006, 116, 1, pp. 237-248.
Hsieh, P.C., C. MacGillivray, J. Gannon, F.U. Cruz and R.T. Lee, "Local controlled intramyocardial delivery of platelet-derived growth factor improves postinfarction ventricular function without pulmonary toxicity," Circulation, 2006, 114, pp. 637-644.
Zymek, P., M. Bujak, K. Chatila, A. Cieslak, G. Thakker, et al., "The role of platelet-derived growth factor signaling in healing myocardial infarcts," Journal of the American College of Cardiology, 2006, 48, 11, pp. 2315-2323.
Grayson, A.C., G. Voskerician, A. Lynn, J.M. Anderson, et al., "Differential degradation rates in vivo and in vitro of biocompatible poly(lactic acid) and poly(glycolic acid) homo- and co-polymers for a polymeric drug-delivery microchip," J Biomater Sci Polymer Edn, 2004, 15, 10, pp. 1281-1304.
Lee, S., M.S. Kim, J.S. Kim, H.J. Park, J.S. Woo, et al., "Controlled delivery of a hydrophilic drug from a biodegradable microsphere system by supercritical anti-solvent precipitation technique," Journal of Microencapsulation, 2006, 23, 7, pp. 741-749.
Jin, Q., M. Zhao S.A. Webb, J.E. Berry, M.J. Somerman, et al., "Cementum engineering with three-dimensional polymer scaffolds," J Biomed Mater Res, 2003, 67A, pp. 54-60.
Faisant, N., J. Siepmann, J.P. Benoit, "PLGA-based microparticles: elucidation of mechanisms and a new, simple mathematical model quantifying drug release," European Journal of Pharm Sci, 2002, 15, pp. 355-366.
Zolnik, B.S., P.E. Leary, D.J. Burgess, "Elevated temperature accelerated release testing of PLGA microspheres," Journal of Controlled Release, 2006, 112, pp. 293-300.
Ramseir, CA, Z.R. Abramson, Q. Jin, W.V. Giannobile, "Gene Therapeutics for Periodontal Regenerative Medicine," Dent Clin North Am, 2006, 50, pp. 245-263.
Luginbuehl, V., L. Meinel, H. P. Merkle and B. Gander, "Localized delivery of growth factors for bone repair," European Journal of Pharmaceutics and Biopharmaceutics, 2004, 58, pp. 197-208.
Rose, F.R.A.J., Q. Hou and R.O.C. Oreffo, "Delivery systems for bone growth factors—the new players in skeletal regeneration," Journal of Pharmacy and Pharmacology, 2004, 56, pp. 415-427.
Seeherman, H., J. Wozney and R. Li, "Bone Morphogenetic Protein Delivery Systems," Spine 2002, 27 (16S), pp. S16-S23.
Uludag, H., D. D'Augusta, R. Palmer, G. Timony and J. Wozney, "Characterization of rhBMP-2 pharmacokinetics implanted with biomaterial carriers in the rat ectopic model," J Biomed Mater Res, 1999, 46, pp. 193-202.
Uludag, H., W. Friess, D. Williams, T. Porter, G. Timony, D. D'Augusta, C. Blake, R. Palmer R, B. Biron and J. Wozney J., "rhBMP—Collagen Sponges as Osteoinductive Devices: Effects of in Vitro Sponge Characteristics and Protein pI on in Vivo rhBMP Pharmacokinetics," Annals of N Y Acad Sci, 1999, 875, 369-378 (7 printed pages).
Zhang, R., D. Xu, T. Landeryou, C. Toth, N. Dimaano, J. Berry, J. Evans and M. Hawkins, "Ectopic bone formation using osteogenic protein-1 carried by a solution precipitated hydroxyapatite," J Biomed Mater Res 2004, 71A, pp. 412-418.
Hollinger, J.O. And K. Leong, "Poly(alpha-hydroxy acids): Carriers for bone morphogenetic proteins," Biomaterials 1996, 17, No. 2, pp. 187-194.
Wei, G., G.J. Pettway, L.K. McCauley and P.X. Ma, "The release profiles and bioactivity of parathyroid hormone from poly(lactic-co-glycolic acid) microspheres," Biomaterials, 2004, 25, 2, pp. 345-352.
Wei, G., Q. Jin, W.V. Giannobile and P.X. Ma, "Nano-fibrous scaffold for controlled delivery of recombinant human PDGF-BB," Journal of Controlled Release, 2006, 112, pp. 103-110.
Wei, G. And P.X. Ma, "Macro-porous and nanofibrous polymer scaffolds and polymer/bone-like apatite composite scaffolds generated by sugar spheres," Journal of Biomedical Materials Research, 2006, 78, pp. 306-315.
Jin, Q., H. Takita, T. Kohgo, K. Atsumi, H. Itoh and Y. Kuboki, "Effects of geometry of hydroxyapatite as a cell substratum in BMP-induced ectopic bone formation," Journal of Biomedical Materials Research, 2000, 51, 3, pp. 491-499.
Miyamoto, S., K. Takaoka, T. Okada, H. Yoshikawa, J. Hashimoto, S. Suzuki and K. Ono, "Evaluation of Polylactic Acid Homopolymers as Carriers for Bone Morphogenetic Protein," Clinical Orthopaedics and Related Research, 1992, 278, pp. 274-285.
Ziegler, J., U. Mayr-Wohlfart, S. Kessler, D. Breitig and K.P. Gunther, "Adsorption and release properties of growth factors from biodegradable implants," Journal of Biomedical Materials Research, 2002, 59, 3, pp. 422-428.
Meinel, L., R. Fajardo, S. Hofmann, R. Langer, J. Chen, B. Snyder, G. Vunjak-Novakovic and D. Kaplan, "Silk implants for the healing of critical size bone defects," Bone, 2005, 37, 5, pp. 688-698.
Woo, B.H., B.F. Fink, R. Page, J.A. Schrier, Y.W. Jo, G. Jiang, M. DeLuca, H.C. Vasconez and P.P. DeLuca, "Enhancement of bone growth by sustained delivery of recombinant human bone morphogenetic protein-2 in a polymeric matrix," Pharmaceutical Research, 2001, 18, 12, pp. 1747-1753.
Lee, J.Y., S.H. Nam, S.Y. Im, Y.J. Park, Y.M. Lee, Y.J. Seol, C.P. Chung and S.J. Lee, "Enhanced bone formation by controlled growth factor delivery from chitosan-based biomaterials," Journal of Controlled Release, 2002, 78, 1-3, pp. 187-197.
Jansen, J.A., J.W.M. Vehof, P.Q. Ruhe, H. Kroeze-Deutman, Y. Kuboki, H. Takita, E.L. Hedberg and A.G. Mikos, "Growth factor-loaded scaffolds for bone engineering," Journal of Controlled Release, 2005, 101, 1-3, pp. 127-136.
Jin, Q., O. Anusaksathien, S.A. Webb, M.A. Printz and W.V. Giannobile, "Engineering of tooth-supporting structures by delivery of PDGF gene therapy vectors," Molecular Therapy, 2004, 9, 4, pp. 519-526.
Anusaksathien, O., S.A. Webb, Q. Jin and W.V. Giannobile, "Platelet-derived growth factor gene delivery stimulates ex vivo gingival repair," Tissue Engineering, 2003, 9, 4, pp. 745-756.
Yamamoto M., Y. Tabata, L. Hong, S. Miyamoto, N. Hashimoto and Y. Ikada, "Bone regeneration by transforming growth factor beta 1 released from a biodegradable hydrogel," Journal of Controlled Release, 2000, 64, 1-3, pp. 133-142.
Tamura, S., H. Kataoka, Y. Matsui, Y. Shionoya, K. Ohno, K.I. Michi, K. Takahashi and A. Yamaguchi, "The effects of transplantation of osteoblastic cells with bone morphogenetic protein (BMP)/carrier complex on bone repair," Bone, 2001, 29, 2, pp. 169-175.
Whang, K., T.K. Goldstick and K.E. Healy, "A biodegradable polymer scaffold for delivery of osteotropic factors," Biomaterials, 2000, 21, 24, pp. 2545-2551.
Richardson, T.P., M.C. Peters, A.B. Ennett and D.J. Mooney, "Polymeric system for dual growth factor delivery," Nature Biotechnology, 2001, 19, 11, pp. 1029-1034.
Sohier, J., R.E. Haan, K. de Groot and J.M. Bezemer, "A novel method to obtain protein release from porous polymer scaffolds: emulsion coating," Journal of Controlled Release, 2003, 87, 1-3, pp. 57-68.
International Search Report for S.N. PCT/US2008/050785 dated Apr. 22, 2008 (5 pages).
Kaplan, D.R., F.C. Chao, C.D. Stiles, H.N. Antoniades and C.D. Scher, "Platelet alpha granules contain a growth factor for fibroblasts," Blood, 1979, 53, pp. 1043-1052 previously filed on Feb. 23, 2009.
Preliminary Examination Report on Patentabity for International Appln. No. PCT/US2008/050785 dated Jul. 23, 2009 (7 pages).

\* cited by examiner

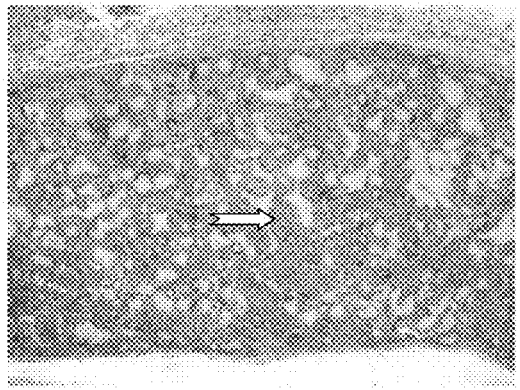 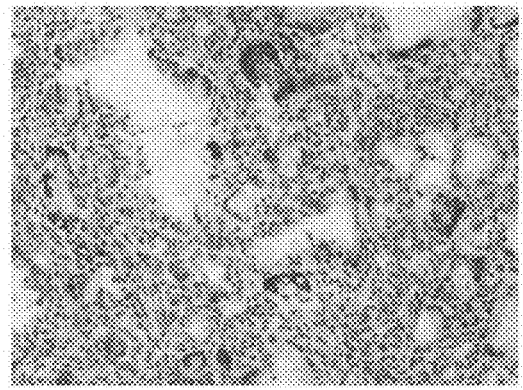
FIG. 4A        FIG. 4B
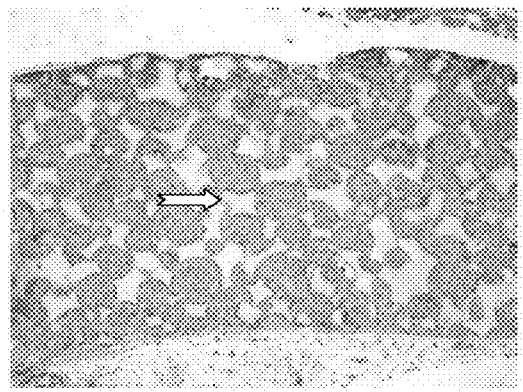 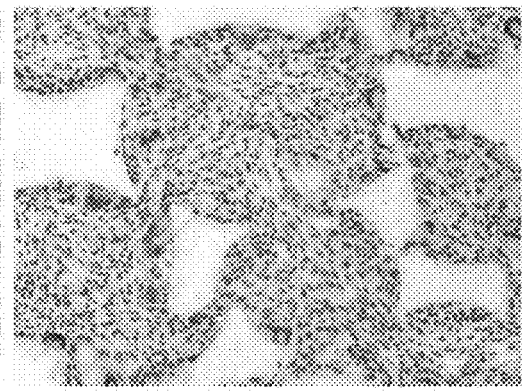
FIG. 4C        FIG. 4D
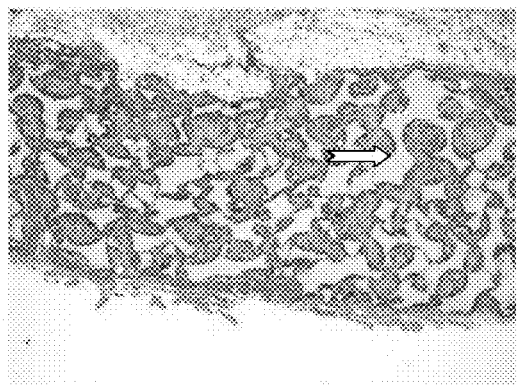 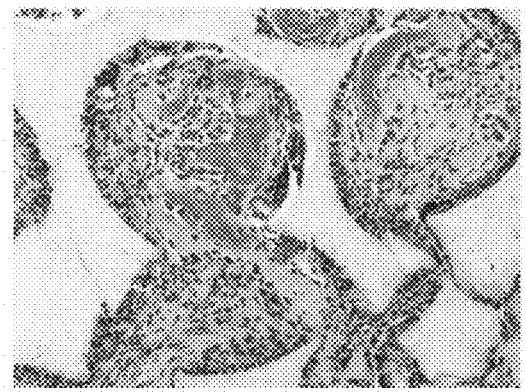
FIG. 4E        FIG. 4F

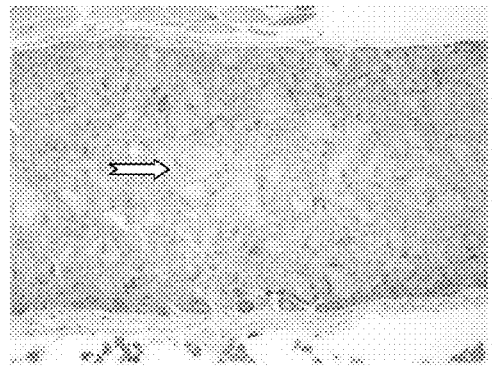
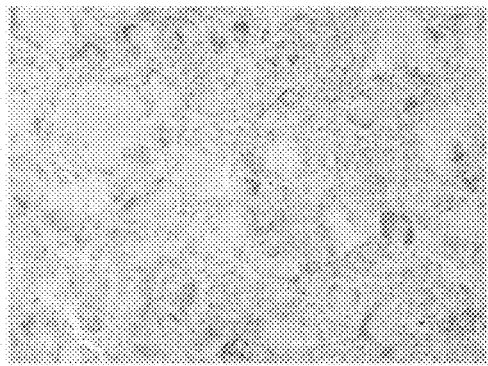
FIG. 6A    FIG. 6B
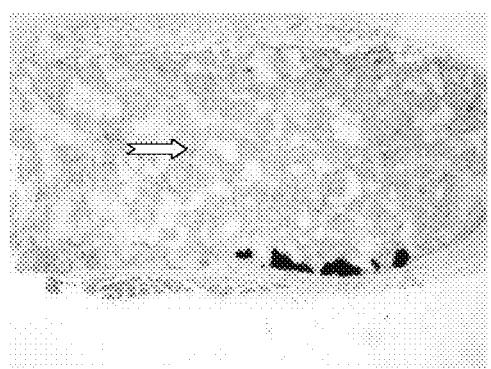
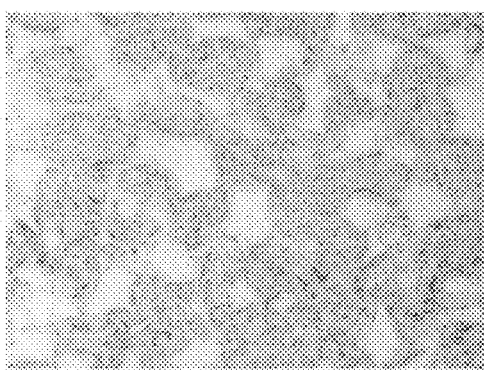
FIG. 6C    FIG. 6D
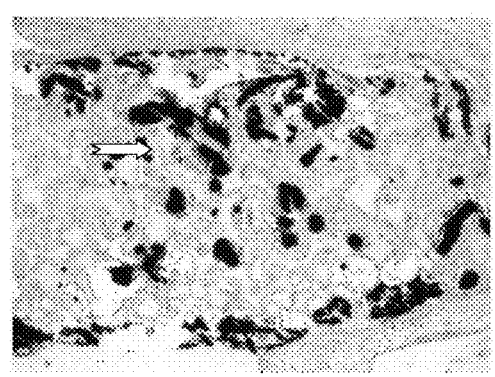
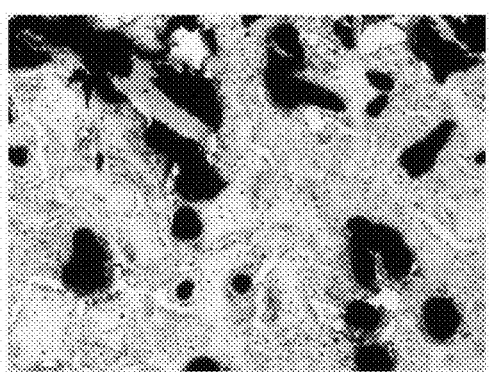
FIG. 6E    FIG. 6F

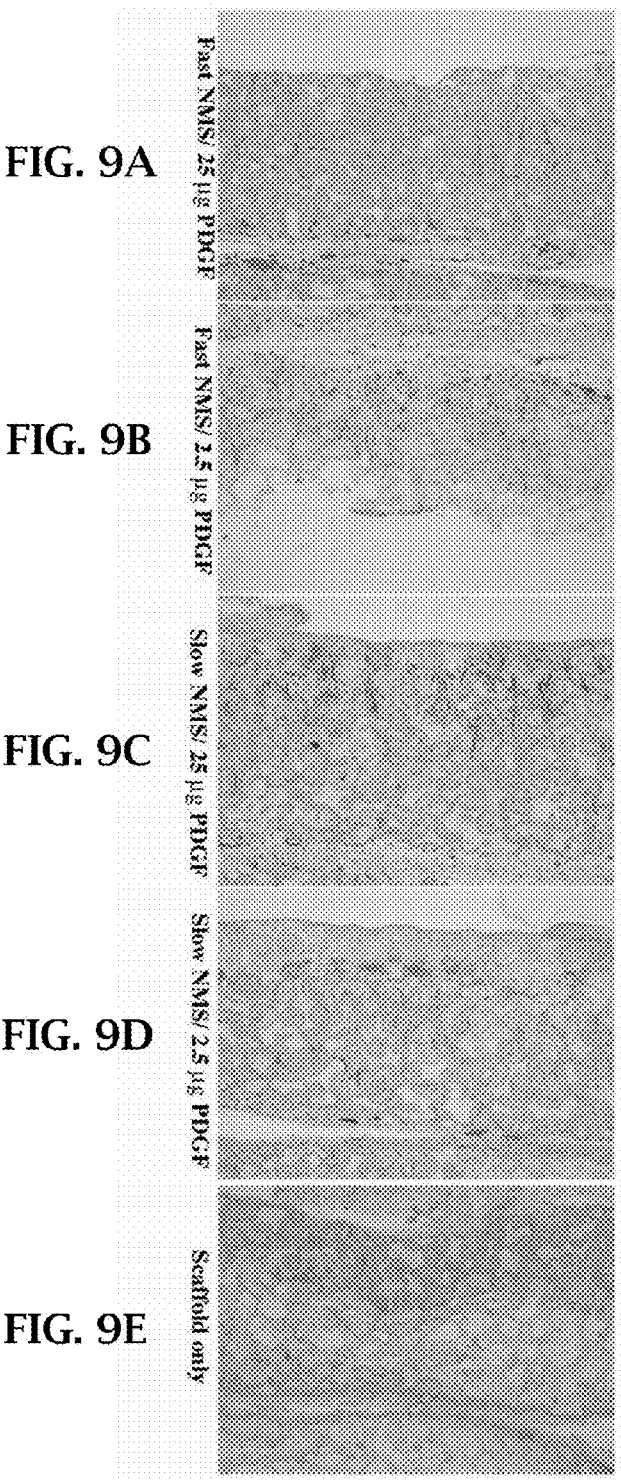
FIG. 9A  Fast NMS/ 25 µg PDGF
FIG. 9B  Fast NMS/ 2.5 µg PDGF
FIG. 9C  Slow NMS/ 25 µg PDGF
FIG. 9D  Slow NMS/ 2.5 µg PDGF
FIG. 9E  Scaffold only

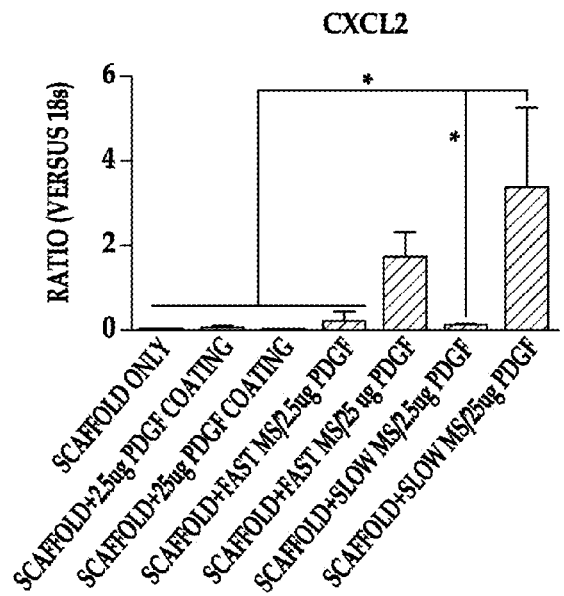
FIG. 15B
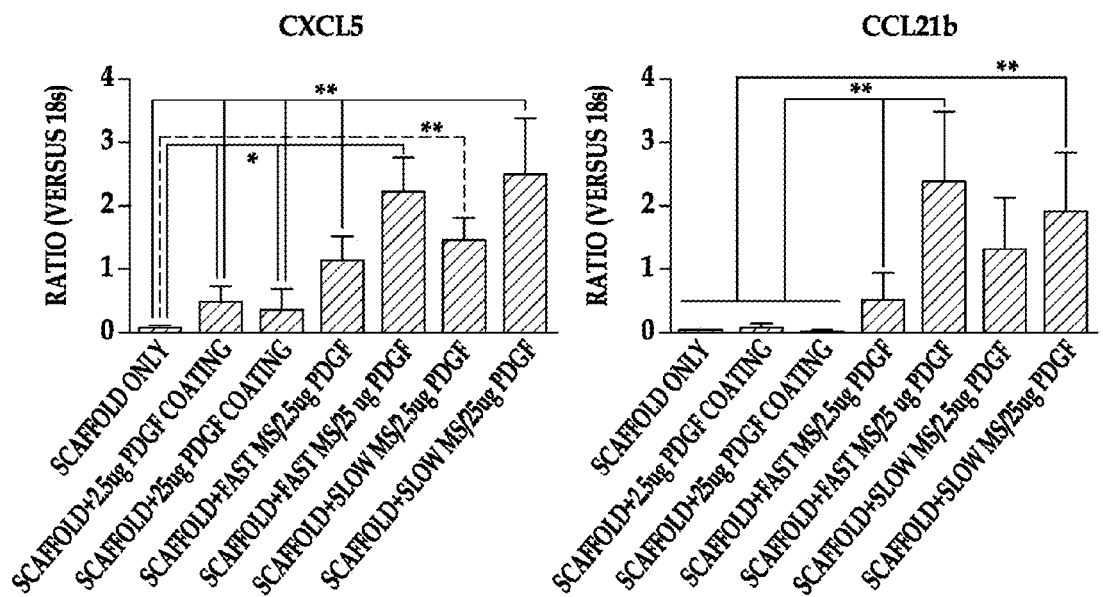
FIG. 15C
FIG. 15D

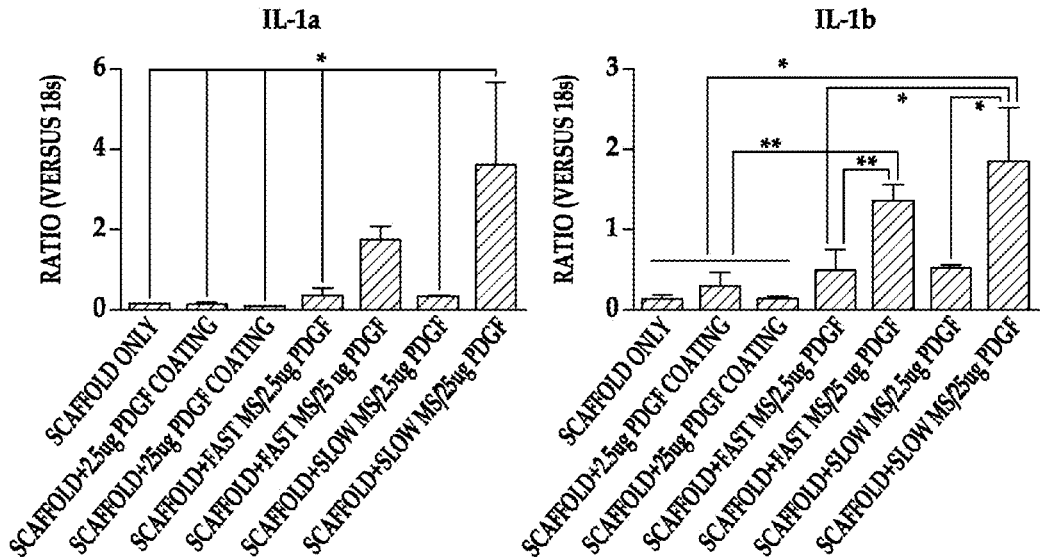
FIG. 16A  FIG. 16B
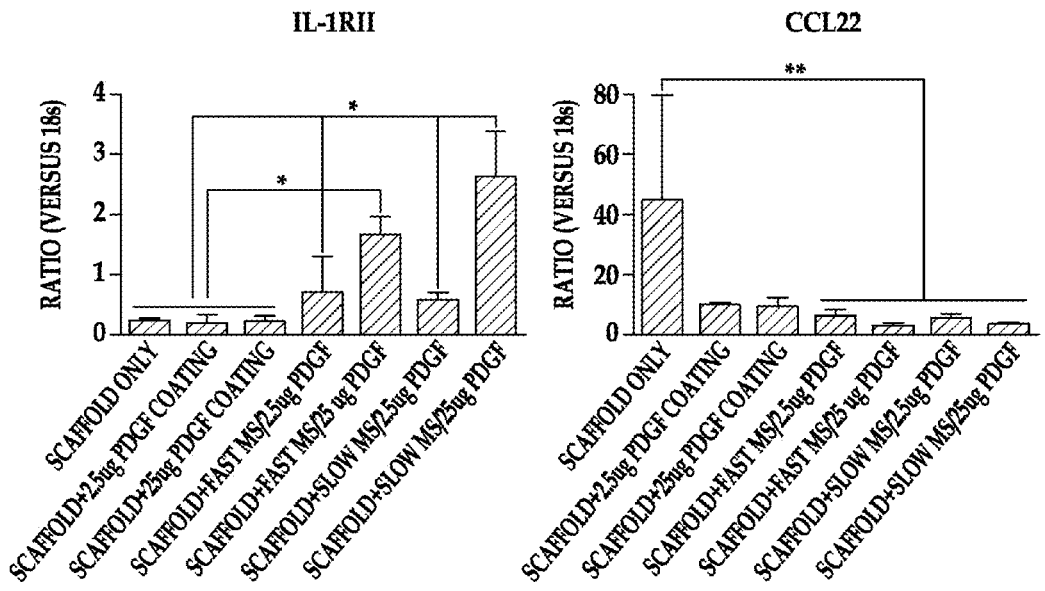
FIG. 16C  FIG. 16D

SEQUENCE LISTING

<160> NUMBER OF SEQ ID NOS: 5

<210> SEQ ID NO 1
<211> LENGTH: 25
<212> TYPE: DNA
<213> ORGANISM: Artificial Sequence
<220> FEATURE:
<223> OTHER INFORMATION: Synthetic

<400> SEQUENCE: 1
ttgtccaaaa gatgctaaag ggtgt                                             25

<210> SEQ ID NO 2
<211> LENGTH: 25
<212> TYPE: DNA
<213> ORGANISM: Artificial Sequence
<220> FEATURE:
<223> OTHER INFORMATION: Synthetic

<400> SEQUENCE: 2
tccaaaagat actgaacaaa ggcaa                                             25

<210> SEQ ID NO 3
<211> LENGTH: 25
<212> TYPE: DNA
<213> ORGANISM: Artificial Sequence
<220> FEATURE:
<223> OTHER INFORMATION: Synthetic

<400> SEQUENCE: 3
gagctcaagc tgctcctttc tcggc                                             25

<210> SEQ ID NO 4
<211> LENGTH: 25
<212> TYPE: DNA
<213> ORGANISM: Artificial Sequence
<220> FEATURE:
<223> OTHER INFORMATION: Synthetic

<400> SEQUENCE: 4
gctccaaagg ctgcaagggg actga                                             25

<210> SEQ ID NO 5
<211> LENGTH: 10
<212> TYPE: DNA
<213> ORGANISM: Artificial Sequence
<220> FEATURE:
<223> OTHER INFORMATION: Synthetic

<400> SEQUENCE: 5
gggaatttcc                                                              10

POROUS OBJECTS HAVING IMMOBILIZED ENCAPSULATED BIOMOLECULES

CROSS-REFERENCE TO RELATED APPLICATIONS

This application claims the benefit of U.S. Provisional Patent Application Ser. No. 60/884,283 filed Jan. 10, 2007 and U.S. Provisional Patent Application Ser. No. 60/896,107 filed Mar. 21, 2007, each of which is incorporated herein by reference in its entirety.

STATEMENT REGARDING FEDERALLY SPONSORED RESEARCH OR DEVELOPMENT

This invention was made in the course of research supported by grants from the National Institutes of Health (NIH) and the National Institute of Dental and Craniofacial Research (NIDCR), Grant Nos. DE015384, DE014755 and DE017689. The U.S. government has certain rights in the invention.

REFERENCE TO A SEQUENCE LISTING

A sequence listing pursuant to 37 CFR §1.821 is submitted herewith.

BACKGROUND

The present disclosure relates generally to controlled release therapeutic objects, and more particularly to such objects formed from porous materials having immobilized encapsulated biomolecules.

Various accidents and diseases result in severe tissue loss and organ failures. For example, in dentistry, periodontal disease afflicts over 50% of the adult population in the United States, with approximately 10% displaying severe disease concomitant with early tooth loss. This disease is often marked by destruction of periodontal support (i.e., periodontal ligament (PDL), cementum and bone). The recognition that periodontal regeneration can be achieved, including formation of new bone, new cementum and supportive PDL, has resulted in increased attempts to develop regenerative therapies.

Bone morphogenetic proteins (BMPs) are suitable for use in bone development and regeneration. Such proteins have been demonstrated to elicit new bone formation both at orthotopic and ectopic sites in experimental animal models. Recombinant BMPs are believed to hold great promise for healing bone fractures, bridging bone nonunions, preventing osteoporosis, and treating periodontal defects.

While BMPs have great potential, exogenous administration of BMPs in a buffer solution does not insure satisfactory new bone induction, especially in higher mammals. The rapid diffusion of BMPs away from application site and the loss of bioactivity leads, in some instances, to insufficient local induction, incomplete bone regeneration, or failure of bone regeneration.

Delivery of BMPs from collagen matrices has been successful in preclinical and human clinical trials; however, disadvantages are still present. Using this technique, it may be difficult to retain the BMPs formulated in a collagen matrix for a sufficient duration, which may result in greater loading and response variability in vivo. In addition, the biodegradability and three-dimensional structures of a collagen matrix are difficult to control. Since BMPs are physically entrapped within collagen, the capability of control over release kinetics from the collagen matrix may be limited. As such, collagen may not be appropriate for applications where varying release rate is desirable. Issues in terms of immunogenicity and disease transmission may also be of concern when using collagen.

Another of the existing regenerative therapies is the use of grafting materials. Grafting materials include autografts (tissues from the same individual), allografts (tissues from human cadavers and bone banks), xenografts (tissues from a different species), and alloplasts ("inert" synthetic materials). Major concerns regarding the use of autografts are the potentially inadequate size and shape. Major concerns regarding the use of allografts and xenografts are the risk of long-term foreign body reaction, limited new bone formation, limited gain of clinical attachment level, the risk of pathogen transmission and immune rejection, and combinations thereof.

Guided-tissue-regeneration (GTR) membranes have also been used either alone or in combination with graft materials. The principle of GTR is to provide an environment that allows the appropriate cells (i.e., those that can enhance formation of periodontal tissues) to repopulate the wound site while excluding cells that may impair periodontal wound healing (e.g., epithelial cells). This is accomplished by placing a barrier over the periodontal defect, thereby preventing cells from the surrounding gingival and epithelium tissues from migrating into the defective sites, and allowing the desired cells (such as PDL fibroblasts, cementoblasts, osteoblasts, or their progenitor cells) to populate the sites. Although significant restoration may be achieved with GTR therapy, with or without the use of graft materials, results are not predictable, and complete regeneration of periodontal defects may not be achieved. This may likely be due to the inherent limitations in the GTR approach, which, in part, relies passively on the natural wound healing process.

BRIEF DESCRIPTION OF THE DRAWINGS

Features and advantages of embodiments of the present disclosure will become apparent by reference to the following detailed description and drawings, in which:

FIGS. 4A through 4F depict microscopic observations of the H & E stained tissue sections of scaffolds retrieved 3 weeks after implantation, where FIGS. 4A and 4B depict control scaffolds, FIGS. 4C and 4D depict 5 µg rhBMP-7 adsorbed to scaffold, FIGS. 4E and 4F depict 5 µg rhBMP-7 incorporated in NS-scaffold, Original magnifications: (FIGS. 4A, 4C, 4E) 40× for full cross sections, and (FIGS. 4B, 4D, 4F) 200× for high magnification views of selected representative areas (arrows point to the selected areas in 4A, 4C, and 4E);

FIGS. 5A and 5B depict control scaffolds, FIGS. 5C and 5D depict 5 µg rhBMP-7 adsorbed to scaffold, FIGS. 5E and 5F depict 5 µg rhBMP-7 incorporated in NS-scaffold, Original magnifications: (FIGS. 5A, 5C, 5E) 40× full cross sections, and (FIGS. 5B, 5D, 5F) 200× for high magnification views of selected representative areas (arrows point to the selected areas in FIGS. 5A, 5C, and 5E);

FIGS. 6A through 6F depict microscopic observations of the von Kossa stained tissue sections of scaffolds retrieved 6 weeks after implantation, where FIGS. 6A and 6B depict control scaffolds, FIGS. 6C and 6D depict 5 µg rhBMP-7 adsorbed to scaffold, and FIGS. 6E and 6F depict 5 µg rhBMP-7 incorporated in NS-scaffold, Original magnifications: (FIGS. 6A, 6C, 6E) 40× and (FIGS. 6B, 6D, 6F) 100× (arrows point to the selected areas in FIGS. 6A, 6C, and 6E); in order to conduct von Kossa staining, the engineered tissue samples were not decalcified and the sectioning resulted in some artifacts, which appear in the H & E histology (multiple cracks in the highly mineralized constructs, i.e., FIGS. 6E & 6F);

FIGS. 9A through 9E are cross sections through the diameters of circular shaped disks of scaffold specimens harvested at 7 days after subcutaneous implantation in a rat ectopic model (histological evaluation of angiogenesis using Factor VIII staining and hematoxylin counterstaining), there was minimal blood vessel formation in control scaffolds without PDGF (FIG. 9E), there was more pronounced blood vessel formation in scaffolds with NMS containing 25 µg of PDGF (FIGS. 9A and 9C) than in those with NMS containing 2.5 µg of PDGF (FIGS. 9B and 9D);

FIGS. 11A-11D show that a portion of scaffold containing no PDGF or a PDGF coating is occupied by ingrown tissue, and FIGS. 11E and 11F show that tissues (fibroblast-like cells and lymphocyte-like cells) completely penetrated the entire scaffold of the scaffolds containing PDGF encapsulated in PLGA microspheres, the scale in the Figures indicates 0.5 mm;

FIGS. 15A through 15D are graphs depicting Chemokine gene induction in PDGF encapsulated microspheres in vivo, where FIG. 15A illustrates CXCL1 gene expression, FIG. 15B illustrates CXCL2 gene expression, FIG. 15C illustrates CXCL5 gene expression, FIG. 15D illustrates CCL21b gene expression, * represents statistically significant differences p<0.01, and ** represents statistically significant differences p<0.05; and FIGS. 16A through 16D are graphs depicting Interleukin 1 (IL-1) and CCL22 gene expressions induced with PDGF encapsulated microspheres in vivo, wherein FIG. 16A illustrates IL-1a gene expression, FIG. 16B illustrate IL-1b gene expression, FIG. 16C illustrate IL-1 receptor type II gene expression, FIG. 16D illustrate CCL22 gene expression, * represents statistically significant differences p<0.01, and ** represents statistically significant differences p<0.05.

DETAILED DESCRIPTION

Figure 1A:
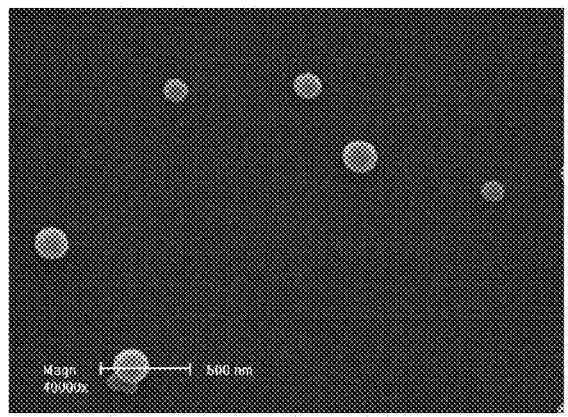
FIGS. 1A through 1F depict the characterization of poly (lactic-co-glycolic acid 50-60K (PLGA50-64K) nanospheres and nanospheres incorporated into poly(L-lactic acid) (PLLA) nano-fibrous scaffolds, where FIG. 1A is a scanning electron micrograph (SEM) of recombinant human BMP-7 (rhBMP-7) containing PLGA50-64K nanospheres, FIG. 1B includes macroscopic photographs of PLLA scaffolds before (left) and after (right) nanosphere incorporation, FIGS. 1C and 1D are SEMs of PLLA nano-fibrous scaffolds before nanosphere incorporation at 100× magnification (1C) and 10,000× magnification (1D), FIGS. 1E and 1F are SEMS of PLLA nano-fibrous scaffolds after PLGA50-64K nanosphere incorporation at 100× magnification (FIG. 1E) and 10,000× magnification (FIG. 1F)

Embodiments of the porous objects disclosed herein advantageously include an effective tissue engineering scaffold that adequately immobilizes biomolecules (e.g., microspheres and/or nanospheres including BMPs, or angiogenic and/or mitogenic factors), temporally and spatially controls release of the biomolecules in vivo, presents interconnected porosity for vascularization and new bone and/or soft tissue induction, induces gene expression, and degrades substantially without soliciting unexpected side effects. It is believed that the highly interconnected porous structure of the scaffold and the sustained release of the biomolecule (e.g., bioactive rhBMP-7, platelet-derived growth factor (PDGF)) contribute to inducing ectopic bone and/or tissue formation throughout the scaffold. Embodiment(s) of the porous object disclosed herein may be used as a delivery system for multiple bioactive factors or as inductive tissue engineering scaffolds for cellular activities, including various tissue regeneration applications.

The porous objects disclosed herein are suitable for in vivo tissue repair/formation. Applications in which such objects may be used include periodontal applications, orthopedic applications (e.g., fusions (i.e., foot and ankle), fractures, etc.), spine applications (including, for example, vertebral compression fractures and spine fusions), sports medicine applications (including, for example, the treatment of tendons (i.e., rotator cuff injury, tendon rupture, tendonosis, tendonitis), ligaments, and cartilage), and/or the like, and/or combinations thereof. Furthermore, the porous object disclosed herein may be suitable for inducing in vivo gene expression. As such, some of the embodiments disclosed herein offer accurate control over biomolecule release to promote soft tissue engineering in vivo.

Generally, an embodiment of the porous object includes a porous material having internal pore surfaces and external pore surfaces, and releasing material encapsulated biomolecules immobilized on one or more of the internal pore surfaces, one or more of the external pore surfaces, or combinations thereof. The releasing material encapsulated biomolecules may be in the form of microspheres and/or nanospheres.

In an embodiment, the porous materials are macro structures including nano-features (e.g., nano-fibrous pore walls instead of solid pore walls), micro-features (e.g., micro-fibrous or micro-porous pore walls), and/or combinations thereof. It is to be understood that, as defined herein, nano-features are intended to include features ranging in size between about $10^{-10}$ meters and about $10^{-6}$ meters; and micro-features are intended to include features ranging in size between about $10^{-6}$ meters and about $10^{-3}$ meters. The macro structures generally include interconnected macro pores. Such macro pores have a size (e.g., diameter) ranging from about $10^{-3}$ meters to about $10^{-1}$ meters. It is believed that the nano-features and/or micro-features may increase the porous material porosity to about 98%.

In another embodiment, the porous materials are macro porous structures including interconnected macro pores with smooth pore surfaces (i.e., "solid-walled" porous materials).

The porous material may be fabricated as part of the method disclosed herein, or it may be a pre-fabricated porous material. In an embodiment, the porous material(s) is/are formed via the combination of phase separation and leaching techniques (e.g., sugar-leaching, paraffin leaching, etc.).

An object may be used to form the porous material. The object may be formed by any suitable manual or automated processing methods. As a non-limitative example, the object (e.g., a sugar sphere porogen or a paraffin sphere porogen) is formed via non-surfactant emulsification, solvent extraction, and freeze-drying. As an alternate, air-drying may be used to dry the object. Without being bound to any theory, it is believed that the surface morphology of the object may change when different drying techniques are implemented. For example, freeze-drying may result in a nano- or micro-featured surface morphology while air-drying may not achieve the same pore surface morphology. As such, the drying technique may be selected, depending, at least in part, on the desired surface morphology of the porous material to be formed.

A material (that will form the porous material) is introduced/cast into and/or onto the object. It is to be understood that the material(s) may include any suitable material(s) for flowing and casting into/onto a mold/object under predetermined conditions. Generally, non-limitative examples of such materials include polymeric materials selected from natural or synthetic hydrophilic polymers, natural or synthetic hydrophobic polymers, natural or synthetic amphophilic polymers, degradable polymers, non-degradable polymers, partially degradable polymers, proteins, polysaccharides, hydrocarbon polymers, lipids, artificial proteins, and/or combinations thereof. More specific non-limiting examples of such materials include poly(L-lactic acid) (PLLA), poly(lactide-co-glycolide) (PLGA), polyglycolic acid (PGA), polyanhydrides, poly(ortho ethers), polycaprolactone, poly(hydroxy butyrate), poly(phosphoesters), poly(propylene fumarate), polyphosphazenes, polycarbonates, polyethylene, polyurethane, glycol (PEG), polyethylene glycol (PEG), polyvinyl alcohol (PVA), gelatin, collagen, alginate, chitin, chitosan, pectin, copolymers thereof, and combinations thereof.

In an embodiment, the material, upon being cast onto the object, substantially conforms to the object.

It is to be understood that a plurality of the objects may be arranged to form an assembly, and the material is cast such that it substantially penetrates areas (e.g., pores) of the assembly between the plurality of objects. The method(s) for forming the assembly may be any suitable methods and/or combinations of methods (e.g., arranging and heating a plurality of objects in a mold). It is to be further understood that the areas of the assembly may be random, uniform, predesigned, and/or combinations thereof. Furthermore, the areas may be assembled using manual processes and/or automated processes.

One non-limiting example of such an assembly is a porogen (a pore-generating material). In this embodiment, predetermined pores/porous structures of suitable size(s) are formed in the material that is cast upon the porogen, resulting in a porous 3-D object. One non-limiting example of predesigned areas in the porogen includes predesigned, interconnected, open pores. In an embodiment in which a porogen is used, the method may further include pre-treating the porogen in water vapor, solvent vapor, water and/or solvent, and/or via heat and/or mechanical loading, and/or combinations of any of these materials/processes to bond at least some of the plurality of objects, thereby forming the interconnects and pores.

After the material is cast onto the object (or plurality of objects, assembly, porogen, etc.), the material may be further manipulated (e.g., via phase separation, solvent evaporation, solvent extraction, freeze-drying, and/or the like, and/or combinations thereof). In an embodiment, phase separation is induced by exposing the material and object to temperatures below freezing. The structures and properties of the porous materials generally depend, at least in part, on the object(s) used, the methods used to form the object(s), type of polymer(s), type of solvent(s), the polymer/solvent systems (e.g., mixture ratio of two or more types of polymer(s) and/or solvent(s)), polymer concentration, the phase-separation conditions (e.g., temperature), etc.

The object(s) is/are then removed from the porous material. Non-limitative examples of such removal processes include dissolving or melting the object, thereby leaving the molded porous material.

As previously stated, embodiments of the porous object include encapsulated biomolecules immobilized on internal and/or external surfaces of the porous material. The biomolecules are selected from bone morphogenetic proteins, TGF-beta proteins, angiogenic factors, mitogenic factors, or combinations thereof. Non-limiting examples of the bone morphogenetic proteins include recombinant human bone morphogenetic protein-2, recombinant human bone morphogenetic protein-7, and combinations thereof. The angiogenic or mitogenic factor is selected from platelet-derived growth factor (PDGF) (non-limiting examples of which include PDGF-AA, PDGF-AB, PDGF-BB, PDGF-CC and PDGF-DD), fibroblast growth factor (FGF) (non-limiting examples of which include acidic and basic FGFs, and related family members), vascular endothelial growth factor (VEGF) and related family members, transforming growth factor-alpha (TGF-α) and related family members, transforming growth factor-beta (TGF-β) and related family members, tumor necrosis factor-alpha (TNF-α) and related family members, hepatocyte growth factor (HGF), interleukin-8, angiogenin, angiopoietin-1, or combinations thereof.

PDGF is a multifunctional growth factor family, composed of A, B, C, and D polypeptide chains which can form homo- or heterodimeric molecules that bind to two structurally related, intrinsic tyrosine kinase receptors (PDGF-Rα and PDGF-Rβ) to exert its biological effects. PDGF advantageously participates in embryonic development of organs such as kidney, heart, and vasculature, and in postnatal tissue repair, regeneration and disease development. Furthermore, PDGF possesses biological functions on cellular chemotaxis, mitogenesis, proliferation, extracellular matrix synthesis, anti-apoptosis and vascularization. PDGF may be particularly suitable for porous objects used in conjunction with soft tissues and osseous tissues.

The biomolecules are encapsulated in any suitable biodegradable or errodable material, such as, for example poly (lactic-co-glycolic acid) (also known as poly(lactide-co-glycolide) (PLGA)). Other suitable examples of the releasing material include, but are not limited to poly(L-lactic acid) (PLLA), polyglycolic acid (PGA), polyanhydrides, poly (ortho ethers), polycaprolactone, poly(hydroxy butyrate), poly(phosphoesters), poly(propylene fumarate), polyphosphazenes, polycarbonates, polyethylene glycol (PEG), polyvinyl alcohol (PVA), polyurethane, collagen, gelatin, alginate, chitin, chitosan, pectin, copolymers thereof, and combinations thereof.

Encapsulation of the biomolecules in the releasing material may be accomplished by a double emulsion technique, a simple emulsion technique, extrusion, phase separation, self-assembly, spray-drying, complexing, blending, chemical reaction or association, or a dendrimer technique. The resulting angiogenic or mitogenic factor containing particles are generally nanospheres, microspheres, or combinations thereof. As previously mentioned, the resulting encapsulated biomolecules are generally in or on nanospheres, microspheres, or combinations thereof.

The encapsulated biomolecules are then immobilized on the internal and/or external surfaces of the porous material. In an embodiment, the encapsulated biomolecules are suspended in a non-solvent or a poor solvent of both the encapsulating material (i.e., the releasing material) and the porous material. The suspension is then added into the porous material. After evaporation of the non-solvent or poor solvent, the releasing material (such as nano/micro particles or spheres) encapsulating the biomolecules are loosely adhered on the internal and/or external pore surfaces of the porous material. By "loosely adhered," it is meant that the biomolecules could be washed away using a non-solvent of the releasing material.

Then, a partial solvent or solvent mixture (e.g., including a solvent and a non-solvent) is added into the porous material with the loosely adhered releasing material encapsulating the biomolecules. Generally, the partial solvent or solvent mixture does not dissolve either the porous material or the releasing material, rather it causes them to adhere by partially dissolving one or both. For different releasing material and porous material combinations, different partial solvents or solvent mixtures are used. For the PLGA releasing materials and PLLA porous materials, non-limiting examples of such solvent mixtures include: cyclohexane/THF (tetrahydrofuran), ratio from about 70:30 by volume to about 95:5 by volume; hexane/THF, ratio from about 70:30 by volume to about 95:5 by volume; cyclohexane/acetone, ratio from about 80:20 by volume to about 95:5 by volume; hexane/acetone, ratio from about 80:20 by volume to about 95:5 by volume; ethanol/acetone, ratio from about 80:20 by volume to about 95:5 by volume; ethanol/THF, ratio from about 70:30 by volume to about 95:5 by volume; isopropanol/THF, ratio from about 70:30 by volume to about 95:5 by volume; isopropanol/acetone, ratio from about 80:20 by volume to about 95:5 by volume; ethanol/chloroform, ratio from about 90:10 by volume to about 95:5 by volume; and ethanol/dichloromethane, ratio from about 90:10 by volume to about 95:5 by volume. The partial solvent(s) or solvent mixture helps the releasing material encapsulating the biomolecules to strongly adhere to the internal and/or external pore surfaces.

After the treatment, the partial solvent(s) or solvent mixture is removed (via freeze-drying, vacuum drying, evaporation, or exchange with a non-solvent for neither the releasing material nor the porous material). This will result in a porous material with strongly adhered releasing material encapsulating the biomolecules on the pore surfaces. By "strongly adhered" is meant that the encapsulated biomolecules could not be easily washed away using a non-solvent or poor solvent of the particles.

Other examples of immobilizing the encapsulated biomolecules on the porous material include high temperature treatments, vapor exposure, or combinations thereof. Non-limitative examples of temperature treatments and vapor exposure are described in U.S. Provisional Patent Application Ser. No. 60/891,985, filed on Feb. 28, 2007, incorporated by reference herein in its entirety.

In any of the embodiments disclosed herein, the amount of biomolecules immobilized on the porous material may be modified. In one embodiment, such a modification is accomplished by increasing or decreasing the concentration of the biomolecule prior to encapsulation. In another embodiment, such a modification is accomplished by increasing or decreasing the amount of the releasing material encapsulating the biomolecules that are seeded/immobilized on the porous materials.

The formed porous object may be implanted into a subject to achieve tissue regeneration and vascularization. It is believed that the polymers used in the porous object are capable of controllably releasing the biomolecules from the releasing material. It is further believed that the release kinetics of the porous object may be modulated by adjusting one or more of the following: the biomolecule loading, the releasing material molecular weight, lactide/glycolide ratio in the PLGA copolymer (when used), and/or formulation methods.

Regarding the releasing material molecular weight, it is believed that high molecular weight polymers degrade slower than those polymers with lower molecular weight. High molecular weight and low molecular weight materials may be selected based on the degradation rate and releasing properties that are desirable for the porous object.

The release kinetics can be further modified by selecting different polymers or copolymers to fabricate the releasing material, as discussed earlier. Different release rates may result in different tissue formation, gene expression, and angiogenesis results. For example, slower release rates may result in better tissue and vasculature formation for some tissues. It is believed, however, that different tissues and defects may respond differently, and thus faster release rates may result in better tissue and vasculature formation for other tissues.

To further illustrate embodiment(s) of the present disclosure, the following examples are given herein. It is to be understood that these examples are provided for illustrative purposes and are not to be construed as limiting the scope of the disclosed embodiment(s).

Example 1

Materials and Methods

Recombinant human bone morphogenetic protein (rhBMP-7) was obtained from Stryker Biotech (Hopkinton, Mass.). Iodination of rhBMP-7 ($^{125}$I-rhBMP-7) was carried out in the Assays and Reagent Facility (Department of Epidemiology) at the University of Michigan. Poly(lactic-co-glycolic acid) (PLGA) copolymers with LA/GA ratio of 50:50 (Medisorb®, PLGA50-6.5K, Mw=6.5 kDa; PLGA50-64K, Mw=64 kDa) and 75:25 (Medisorb®, PLGA75-113K, Mw=113 kDa) were purchased from Alkermes Inc. (Wilmington, Ohio). Poly(L-lactic acid) (PLLA) with an inherent viscosity of 1.6 dl/g was purchased from Boehringer Ingelheim (Ingelheim, Germany). Other chemicals used were: poly(vinyl alcohol) (PVA) (88 mol % hydrolyzed, Mw=25,000) obtained from Polysciences Inc. (Warrington, Pa.); Trifluoroacetic acid (TFA), bovine serum albumin (BSA, Fraction V) and gelatin (type B from bovine skin) from Sigma (St. Louis, Mo.); dichloromethane, cyclohexane, hexane and tetrahydrofuran from Aldrich Chemical Company (Milwaukee, Wis.).

Preparation of Nanosphere-Immobilized Nano-Fibrous Scaffolds (NS-Scaffold)

Lyophilized rhBMP-7 powder was dissolved in 0.1% TFA with 0.1 wt % gelatin and BSA to form a clear aqueous solution. Three PLGA formulations (PLGA50-6.5K, PLGA50-64K and PLGA75-113K) were used to encapsulate rhBMP-7 into nanospheres (NS) utilizing a double emulsion technique. For release kinetics evaluation, radio-labeled $I^{125}$-rhBMP-7 was added during nanosphere preparation as a tracer ($I^{125}$-rhBMP-7: unlabeled rhBMP-7=1:100, total 100 ng rhBMP-7 per mg polymer). RhBMP-7 (5 μg/mg polymer) was encapsulated into PLGA50-64K nanospheres for in vivo study. Gelatin/BSA-containing PLGA nanospheres (blank NS) were prepared as controls.

Macroporous and nano-fibrous PLLA scaffolds were fabricated by the combination of phase separation and sugar-leaching techniques. Highly porous scaffolds were cut into circular disks with dimensions of 7.2 mm in diameter and 2 mm in thickness. The scaffolds were sterilized using ethylene oxide for about 24 hours before the BMP nanospheres were immobilized.

PLGA nanospheres were immobilized onto nano-fibrous PLLA scaffolds using a post-seeding method. The PLGA nanospheres were suspended in a non-solvent. The suspension was seeded onto the prefabricated nano-fibrous PLLA scaffold, and the scaffold was left in air to evaporate the solvent, followed by vacuum drying. The NS-scaffolds were then subjected to a mixed solvent of hexane/THF (volume ratio of 90/10) to immobilize the nanospheres on the scaffold. This was followed by vacuum-drying for about 3 days to remove the solvent. Nanospheres containing gelatin/BSA were also immobilized onto scaffolds for morphological examination and as controls for release kinetics and animal implantation studies. The morphology of the scaffolds before and after nanosphere immobilization was examined using scanning electron microscopy (SEM, Philips XL30 FEG).

In Vitro Release Study

RhBMP-7 release profiles from PLGA nanosphere-immobilized PLLA scaffolds were determined in vitro by radioactivity detection. One NS-scaffold was placed in about 1.0 ml phosphate buffered saline (PBS, 10 mM, pH=7.4 with 0.1% BSA) at 37° C. under orbital shaking at 60 rpm. Supernatant was collected and an equal amount of fresh medium was added to each sample at the designated time points: 1, 3, 5, 7, 10, 14, 21, 28, 35, 42, 49, and 56 days for PLGA50-6.5K NS-scaffolds; 1, 3, 5, 7, 10, 14, 21, 28, 35, 42, 49, 56, 63, and 70 days for PLGA50-64K NS-scaffolds; and 1, 3, 7, 14, 21, 28, 35, 42, 49, 56, 63, and 70 days for PLGA75-113K NS-scaffolds. The radioactivity of collected supernatant was analyzed using a gamma counter (Gamma 5500, Beckman) and converted to calculate the quantity of the released rhBMP-7. Again, scaffolds with gelatin/BSA containing nanospheres were used as controls.

Preparation of Implants

Three groups of scaffold implants were prepared for in vivo study on rats as listed in Table 1. Group I included control scaffolds: PLLA scaffold with PLGA50-64K nanospheres containing gelatin/BSA. Group II included rhBMP-7 adsorbed scaffolds: sterilized PLLA scaffold with PLGA50-64K nanospheres containing gelatin/BSA, 40 μl rhBMP-7 buffer solution (sterile, 5 μg rhBMP-7) were added to the scaffold and air dried at 4° C. Group III included rhBMP-7 NS-scaffolds: PLLA scaffold with PLGA50-64K nanospheres containing 5 μg rhBMP-7. The scaffolds (Groups I and III) were sterilized in 70% ethanol for 30 minutes, lyophilized under sterile conditions and stored at −20° C. until implantation.

TABLE 1

Experiment design of BMP-delivering PLLA scaffolds for ectopic bone induction

| Scaffold group | BMP-7 (μg) | PLGA50-NS |
|---|---|---|
| I | 0 | 64K, with BSA encapsulated |
| II | 5 in buffer* | 64K, with BSA encapsulated |
| III | 5 in NS | 64K, with rhBMP-7 encapsulated |

Three scaffold samples per group were implanted (n = 3).
*10 mM sodium acetate/acetic acid buffer, pH = 4.5

Subcutaneous Implantation

For implantation, male Sprague-Dawley rats with a weight range of 200-250 grams (Charles River Laboratories) were used. Surgery was performed under general inhalation anesthesia with isofluorane. The back of the animals was shaved, washed and disinfected with povidone-iodine. Two midsagittal incisions were made on the dorsa and four subcutaneous pockets were created using blunt dissection. One scaffold was implanted subcutaneously into each pocket. Three samples were implanted for each group (n=3). After placement of the scaffolds, the incisions were closed with staples. The scaffolds were placed alternately at different sites for each rat. At the end of each implantation period (3 or 6 weeks), the rats were sacrificed and the scaffolds were harvested. The animal procedures were performed according to the guidelines approved by the University of Michigan Committee of Use and Care of Laboratory Animals.

Radiographic and Histological Examination

The scaffolds were retrieved at 3 and 6 weeks after subcutaneous implantation. Radiographic analysis was performed for scaffolds using a microradiography system (Faxitron X-ray Corporation, Wheeling, Ill.) at conditions of 35 kV and 60 seconds. The percent radiopacity of scaffold specimen were measured using ImageJ software (NIH, Bethesda, Md.) based on discrimination of gray-level density. In addition, the scaffold specimen was fixed in neutral buffered 10% formalin and then embedded in paraffin. Five-micrometer sections were cut and stained with hematoxylin and eosin (H & E) or von Kossa for light microscopic observation.

Results

Characterization of BMP-7 Nanosphere-Immobilized Scaffolds

RhBMP-7 encapsulated PLGA nanospheres had a high encapsulation efficiency of 78-81% as determined using radioactivity detection. Despite the evaluation of the three different PLGA formulations (PLGA50-6.5K, PLGA50-64K and PLGA75-113K), the nanospheres presented relatively uniform spherical shapes and smooth non-porous surfaces (FIG. 1A). The average diameter of the nanospheres was near 300 nm based on SEM observation.

Figure 1B:
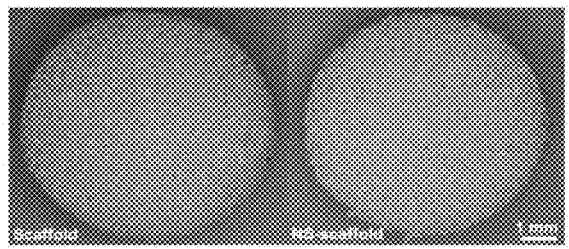
Figure 1C:
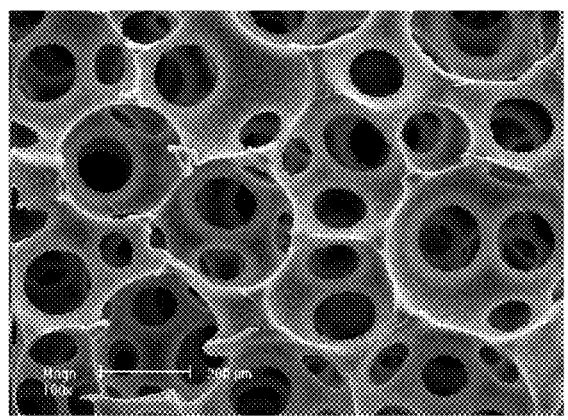
Figure 1D:
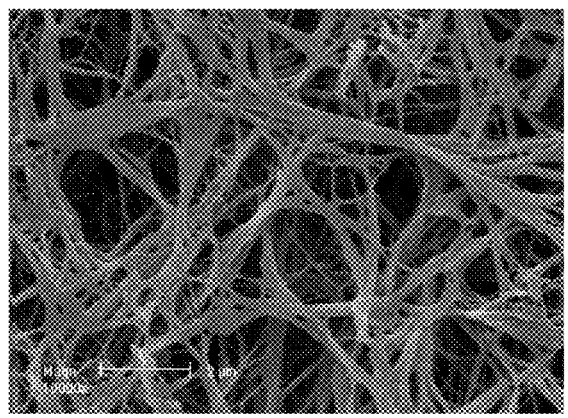

Three-dimensional PLLA macroporous and nano-fibrous scaffolds were prepared with a high porosity of about 98%. The scaffold was characterized with 3D multi-level porous architectures: regular spherical macropores having a diameter ranging from about 250 μm to about 425 μm, interpore openings of about 100 μm, and nano fibers within the pore walls of the scaffold. Furthermore, the diameter of the PLLA nano fibers ranged from about 50 nm to about 500 nm, which is similar to type I collagen fibers in size (FIGS. 1B-1D). The macropores were well interconnected from macro-, micro- to nano levels. It is believed that this contributes to rendering the scaffold conducive for the cellular activity and tissue penetration into the scaffold, and allows for subsequent efficient incorporation of growth factor containing nanospheres.

Figure 1E:
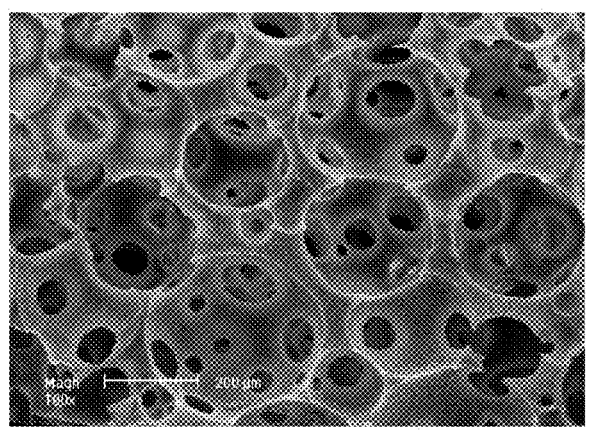
Figure 1F:
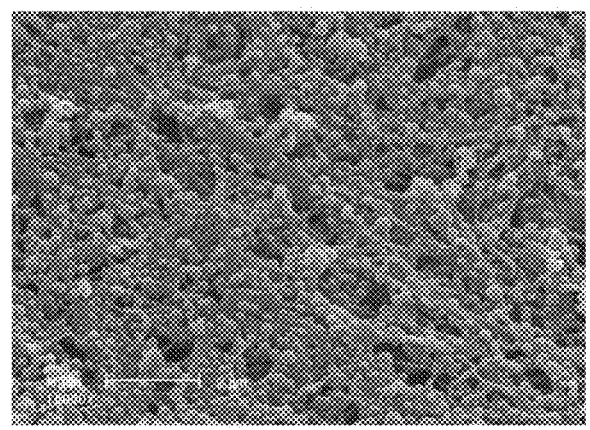

The morphology of nano-fibrous PLLA scaffolds after PLGA50-64K nanosphere incorporation is shown in FIGS. 1E and 1F. Compared to the original PLLA scaffolds before NS incorporation, the spherical macropores (from 250 μm to 425 μm) and interpore openings (about 100 μm) of the NS-scaffolds were well-preserved. The pore walls of the NS-scaffolds presented both nano fibers and nanospheres, the latter of which adhered on nano-fibers and were distributed uniformly throughout the scaffolds.

In Vitro BMP-7 Release Kinetics

Figure 2:
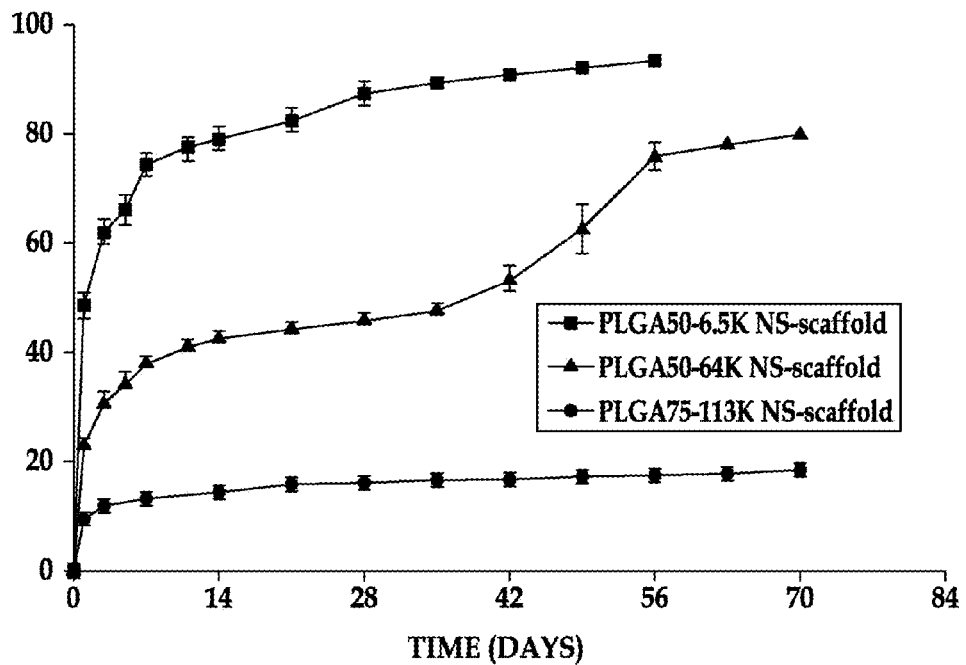
FIG. 2 is a graph depicting the in vitro release kinetics of rhBMP-7 from nanospheres immobilized on nano-fibrous scaffolds (in 10 mM PBS with a BMP-7 loading of 200 ng/scaffold), where each data point represents a mean±standard deviation (n=3)

FIG. 2 shows the rhBMP-7 release profiles from NS-scaffolds in varying temporal patterns. This is due, at least in part, to different PLGA nanosphere immobilization. RhBMP-7 was rapidly released from the PLGA50-6.5K NS-scaffold with a 48% initial burst release in day 1, and 78% of rhBMP-7 released within 2 weeks. PLGA50-64K NS-scaffolds released rhBMP-7 in a multi-phasic release pattern. After an initial burst release of 23% and fast release (1.5% per day) during the first two weeks, rhBMP-7 was subsequently released more slowly (0.3% per day) during the next 3 weeks. From week 5 to week 8, there was a second rapid release of 20% rhBMP-7 (0.98% per day) followed by another slow release. The second rapid release was in accordance with the significant mass loss and disintegration of PLGA nanospheres at that time (data not shown). The PLGA75 NS-scaffold showed a sustained slow release (0.13% per day) for the whole time period investigated after the initial burst release (9.5%).

It is believed that with an increase of molecular weight and/or LA/GA ratio in PLGA copolymer nanospheres, the initial burst release is reduced significantly. A comparison of the release profiles of rhBMP-7 from NS-scaffold with those from nanospheres alone indicated that the overall release patterns were similar in trend (data not shown). These results indicate that the release kinetics of protein from a scaffold is mainly controlled by the release from nanospheres, which can be controlled by tailoring the chemical and/or physical properties of the copolymers used.

Radiographic Analysis

Figure 3A:
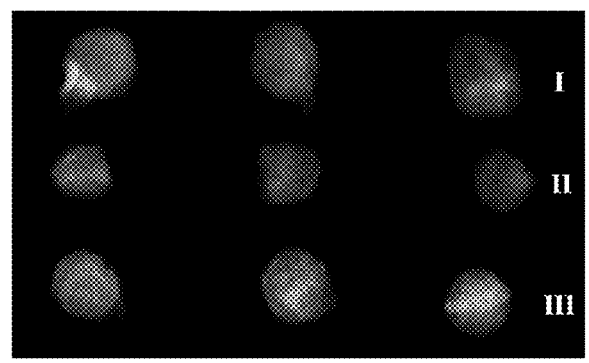
FIGS. 3A through 3D depict radiographic results of retrieved scaffold samples and corresponding bar graphs 3 weeks after implantation (3A and 3B) and 6 weeks after implantation (3C and 3D), in FIGS. 3A and 3C, I=the control scaffolds, II=scaffolds with 5 μg adsorbed rhBMP-7, and III=scaffolds with PLGA50-64K nanospheres containing 5 μg rhBMP-7, in FIGS. 3B and 3D, each data point represents a mean±standard deviation (n=3), * represents statistically significant differences p<0.05; ** represents statistically significant differences p<0.01.
Figure 3C:
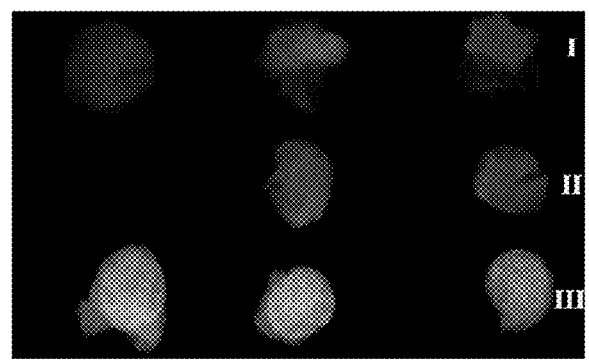
Figure 3B:
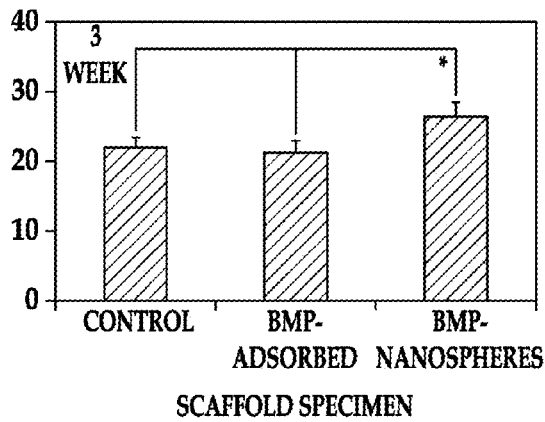
Figure 3D:
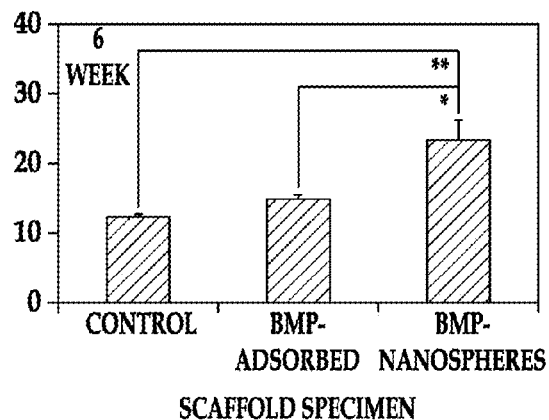

Three weeks after subcutaneous implantation, radiographic examination showed increased radiodensity in the rhBMP-7 NS immobilized scaffolds, but not in the control and rhBMP-7 adsorbed scaffolds. This indicates that ectopic bone formation was induced by rhBMP-7 released from PLGA nanospheres that were immobilized within the porous scaffolds, as shown in FIG. 3A. At 6 weeks, increased radiopacity consistent with newly formed bone was noted throughout the rhBMP-7 NS-scaffolds, while bone formation was scant to non-existent in the control and BMP adsorbed scaffolds. The radiopacity in the rhBMP-7 NS-scaffolds was significantly higher than that formed in the control and rhBMP-7 adsorbed scaffolds (FIG. 3B).

Histologic Analysis

Figure 5A:
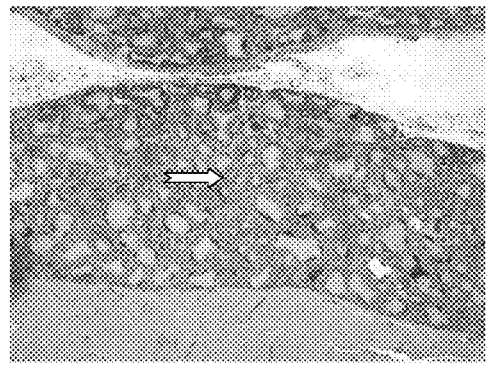
FIGS. 5A through 5F depict microscopic observations of the H & E stained tissue sections of scaffolds retrieved 6 weeks after implantation, where
Figure 5B:
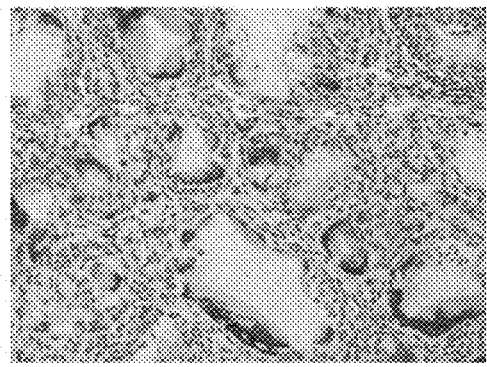
Figure 5C:
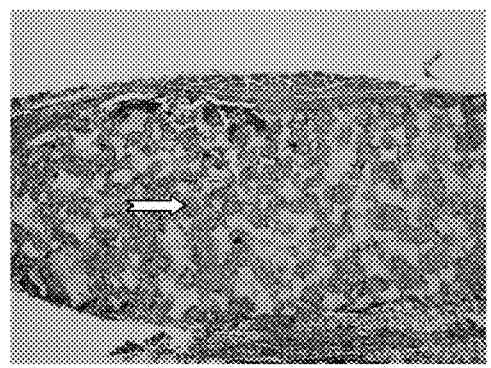
Figure 5D:
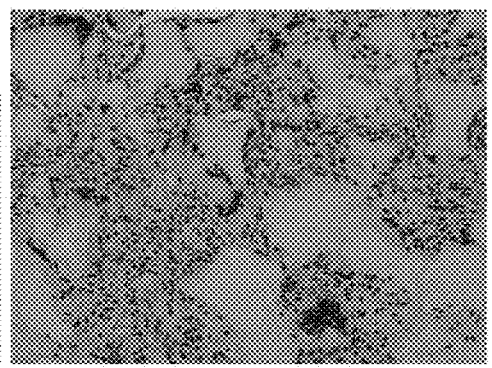
Figure 5E:
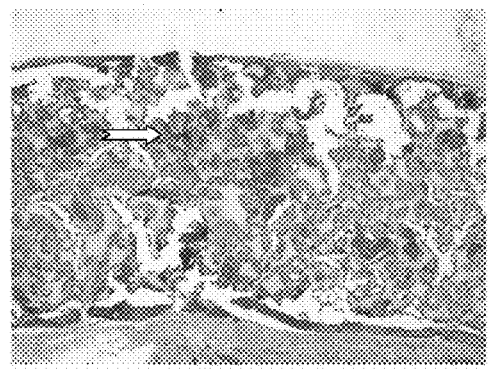
Figure 5F:
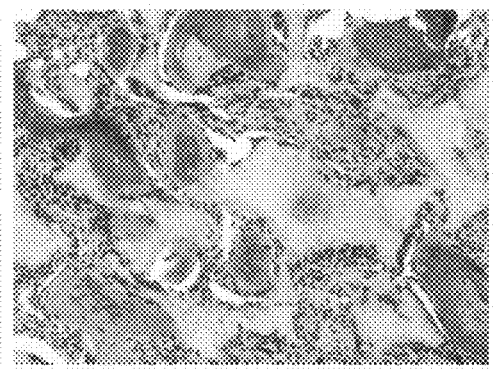

Although cells and tissues penetrated throughout the scaffolds for all groups (I-III) at three weeks, the histological micrographs showed no bone formation in the control and rhBMP-7 adsorbed scaffolds (see FIGS. 4A-4D). These cells were mainly fibroblasts and some multinucleated giant cells. In contrast, new bone consistently formed on the surface of BMP-7 nanosphere immobilized scaffolds (see FIGS. 4E and 4F). The neo-bone was stained pink with H & E staining. After 6 weeks, no bone formation was observed in the control scaffolds, and macrophages accumulated around the polymer matrix (nano-fibrous pore walls) (see FIGS. 5A and 5B). The rhBMP-7 adsorbed scaffolds also failed to induce significant ectopic bone formation (FIGS. 5C and 5D). However, robust bone formation was achieved throughout the rhBMP-7 NS-scaffolds, and the presence of macrophages was minimal (FIGS. 5E and 5F). The newly formed bone in rhBMP-7 NS-scaffolds was mineralized as noted by von Kossa staining (FIGS. 6E and 6F). The results suggest that incorporation of rhBMP-7 into nanospheres (that were then immobilized onto scaffolds) protected the biological activity of rhBMP-7, and delivered the protein locally with prolonged duration to induce ectopic bone formation throughout the scaffold. In contrast, simple adsorption of rhBMP-7 onto the scaffolds failed to induce bone formation in the scaffolds, likely due to significant loss of the biological activity of the BMP-7.

Discussion

In experimental studies that validate the effectiveness of BMPs for the stimulation of bone formation, the need of an efficient delivery system is recognized. The properties of carriers, including material type, geometry, porosity, and pore size, may contribute to the delivery of BMPs and the subsequent success of bone regeneration. In bone tissue engineering, the delivery system should serve two primary roles: to maximize the osteogenic effect of BMPs by maintaining the bioactivity and duration of BMPs at implantation site with an optimal release profile; and to serve as an osteoconductive scaffold with suitable pore structure for vascularization and bone formation. As previously disclosed, embodiments of the porous object including the nanosphere immobilized scaffold advantageously serve these two functions.

As shown in Example 1, RhBMP-7 containing PLGA nanospheres were successfully immobilized onto 3D macroporous and nano-fibrous PLLA scaffolds using a post-seeding technique. By varying the composition and molecular weight of PLGA nanospheres that were immobilized onto the scaffold, rhBMP-7 release times from weeks to months were achieved from the 3D porous tissue engineering scaffold. The rhBMP-7 delivering NS-scaffold has been demonstrated to induce ectopic bone formation throughout the scaffold after subcutaneous implantation in rats.

Embodiments of the porous object disclosed herein offer several advantages over other scaffold delivery systems. First, both PLGA and PLLA are biodegradable and biocompatible polymers that have been widely used for biomedical applications with minimal immunogenicity. Second, PLGA copolymers are commercially available with a variety of LA/GA ratios, molecular weights, and end groups, thus offering great flexibility to adjust release kinetics of encapsulated biomolecules (e.g., growth factors, such as BMPs) from a scaffold. The NS-scaffold system is capable of providing varying biomolecule release rates to satisfy the needs of bone healing and regeneration at different sites and under different conditions. Third, the porous scaffold provides a suitable microenvironment for cellular activity and tissue formation. Furthermore, after immobilization with rhBMP-7 PLGA nanospheres, the NS-scaffolds retain high porosity (98%) and well-interconnected macroporous structures (see FIGS. 1B and 1E). It is believed that the maintenance of interconnected macroporosity provides sufficient spaces for rhBMP-7 to induce new bone formation throughout the scaffold (see FIGS. 5E, 5F, 6E and 6F). Fourth, the pore walls are nano-fibrous. It is believed that the nano-fibrous structures improve bone cell attachment and differentiation, due, at least in part, to the structural similarity to type I collagen fibers, which is a major extracellular matrix (ECM) component of natural bone. In addition, PLLA macroporous and nano-fibrous scaffolds allow uniform bone-like apatite growth in simulated body fluid (SBF), which may provide superior osteoconductivity for bone repair.

FIGS. 3 and 4 illustrate that cells and tissues penetrate into all control, rhBMP-7 adsorbed, and rhBMP-7 NS immobilized scaffolds 3 weeks post subcutaneous implantation. This is due, at least in part, to the use of interconnected porous structures. There was substantial de novo bone formation in the rhBMP-7 NS-scaffold; however, there was little bone formation in the control and rhBMP-7 adsorbed scaffolds. The rhBMP-7 NS-scaffold delivery system advantageously released and localized the rhBMP-7 for a desired duration at the implantation site, thereby substantially ensuring the differentiation of invaded cells into osteoblasts for bone formation.

Embodiments of the present disclosure (in particular those discussed in reference to Example 1) advantageously use both the initial release of the biomolecule and the sustained release of the biomolecule to achieve bone induction and mineralization. As shown in Example 1, the initial level of rhBMP-7 and the sustained local release of the rhBMP-7 contributed to adequate bone induction and mineralization. In contrast, the rhBMP-7 adsorbed NS-scaffold provided either a bolus or a pulse delivery of rhBMP-7 with substantial loss of bioactivity, leading to the failure of bone formation. It is believed that the nanosphere incorporation protected bioactive growth factors from denaturation, which commonly occurs in passive adsorption of growth factors onto biodegradable scaffolds/implants due, at least in part, to conformational changes or degradation under physiological environment. Encapsulation of growth factors into nanospheres that are subsequently immobilized onto scaffolds, has been demonstrated to be a unique and successful strategy to achieve prolonged release of bioactive growth factors from scaffolds for tissue engineering applications.

Example 2

Materials and Methods

Poly(lactic-co-glycolic acid) (PLGA) with LA/GA ratio of 50:50 (Medisorb®, PLGA50-6.5K, Mw=6.5 kDa; PLGA50-64K, Mw=64 kDa) was obtained from Alkermes Inc. (Wilmington, Ohio). Poly(lactic acid) (PLLA) with an inherent viscosity of 1.6 dl/g was obtained from Boehringer Ingelheim (Ingelheim, Germany). Recombinant human platelet-derived growth factor (rhPDGF-BB) was obtained from Biomimetic Therapeutics (Franklin, Tenn.). Dulbecco's Modified Eagle Medium (DMEM) and antibiotics were obtained from Invitrogen Corp. (Carlsbad, Calif.). Other chemicals used were: poly(vinyl alcohol) (PVA) (88 mol % hydrolyzed, MW=25,000) obtained from Polysciences Inc. (Warrington, Pa.); dichloromethane, sodium dodecyl sulfate (SDS), sodium acetate, and acetic acid obtained from Aldrich Chemical Company (Milwaukee, Wis.).

PLGA Nano- and Micro-Sphere (NMS) Preparation

PLGA NMS were fabricated using a double emulsion technique. PDGF-BB buffer solution (PDGF-BB in 20 mM sodium acetate buffer at pH=6.3, varying in concentration of 0, 3, 10, 100, 300, 600, 1000 and 3000 µg/ml) was emulsified into 1 ml of 10% PLGA/dichloromethane solution, using a probe sonicator at 15 W (Virsonic 100, Cardiner, N.Y.) for about 10 seconds over an ice bath to form the primary water-in-oil emulsion. For the implantation study, 100 µl of 3 mg/ml PDGF-BB solution (20 mM sodium acetate, pH=6.3) was emulsified into 1 ml of 10% PLGA/dichloromethane solution. The water-in-oil emulsion was mixed with 20 ml of 1% PVA aqueous solution under sonication to form a water-in-oil-in-water double emulsion. The solution was then stirred magnetically at room temperature for at least 3 hours to evaporate dichloromethane, and centrifuged to collect solid NMS. The resultant NMS containing PDGF-BB were washed twice with distilled water, freeze-dried, and stored in a −80° C. freezer until use. The average diameter of the NMS containing PDGF-BB was determined to be smaller than 1 µm on the order of magnitude of $10^2$ nm using scanning electron microscopy (SEM, Philips XL30 FEG).

Fabrication of PLLA Nano-Fibrous Scaffolds

PLLA macroporous nano-fibrous scaffolds were fabricated by the combination of phase separation and sugar-leaching techniques. About 600 µL of 10% PLLA/THF solution was cast into an assembled sugar template (formed from bound sugar spheres of 250-425 mm in diameter) under mild vacuum. The polymer/sugar composite was phase separated at about −20° C. overnight, and then immersed into cyclohexane to exchange THF for 2 days. The resulting composites were freeze-dried. The sugar spheres were leached out in distilled water, and the composites were freeze-dried again to obtain highly porous scaffolds. The scaffolds were cut into circular disks with dimensions of 7.2 mm in diameter and 2 mm in thickness. The average weight of the porous scaffold ranged from about 2.5 mg to about 3.0 mg.

Incorporation of PLGA NMS into PLLA Nano-Fibrous Scaffolds

PLGA NMS containing PDGF-BB were incorporated into PLLA nano-fibrous scaffolds using a post-seeding method. Dry PLGA NMS were suspended in hexane with a concentration of 5 mg NMS/ml. About 80 µL of the suspension was seeded onto each scaffold, and the scaffold was left in air for 30 minutes to evaporate the hexane. This procedure was repeated until one scaffold contained 2.5 µg or 25 µg PDGF-BB for the implantation study. The calculation was based on 77% encapsulation efficiency of PDGF-BB in the nano- and/ or micro-sphere. The scaffold was then subjected to a mixed solvent of hexane/THF (volume ratio of 90/10) to immobilize the NMS on the scaffold. The scaffold was vacuum-dried for about 3 days to remove the solvent. Controls included the scaffold alone, and scaffolds seeded with NMS without any growth factors.

Tissue Neogenesis in Rat Ectopic Model

In order to investigate the effect of PDGF release rate on PDGF biological function in vivo, nine groups were prepared for the rat ectopic model study. Two release rates achieved by using two different PLGA polymers were investigated in the animal study. One is PLGA (LA/GA=50/50, MW=6.4 kD) to achieve the relatively "fast" release rate, while the other is PLGA (LA/GA=50/50, MW=65 kD) to achieve the relative "slow" release rate. The nine groups included: 1) nanofibrous scaffold only; 2) nanofibrous scaffold and slow NMS without PDGF-BB; 3) nanofibrous scaffold and fast NMS without PDGF-BB; 4) nanofibrous scaffold and 2.5 µg PDGF-BB coating; 5) nanofibrous scaffold and 25 µg PDGF-BB coating; 6) nanofibrous scaffold and fast NMS containing 2.5 µg PDGF-BB; 7) nanofibrous scaffold and fast NMS containing 25 µg PDGF-BB; 8) nanofibrous scaffold and slow NMS containing 2.5 µg PDGF-BB; and 9) nanofibrous scaffold and slow NMS containing 25 µg PDGF-BB.

For implantation, male Sprague-Dawley rats with a weight range of about 200 g to about 250 g (Harlan, Indianapolis, Ind.) were used. Surgery was performed under general inhalation anesthesia with isofluorane. The back of the animals was shaved, washed and disinfected with povidone-iodine. Two midsagittal incisions were made on the dorsa and four subcutaneous pockets were created using blunt dissection. One scaffold was implanted subcutaneously into each pocket. After scaffold placement, the incisions were closed with staples. The scaffolds were placed alternately at different sites for each rat. At the end of each implantation period, the rats were sacrificed and the scaffolds were harvested. The implants were harvested at 3 days, 1, 2, and 3 weeks after implantation.

Histology, Histomorphometry and Histoimmunochemistry

The harvested pellets were fixed in 10% neutral buffered formalin, embedded in paraffin, and cut into 4 or 5 µm thick cross sections along the diameters of the circular disk-shaped specimens. One section was stained with hematoxylin and eosin. Images of specimens were captured using a Nikon Eclipse 50i microscope (Nikon, Inc., Melville, N.Y.) equipped with a Nikon Digital Sight DS U1 camera (Nikon, Inc., Melville, N.Y.) for analysis using Image Pro Plus™ software (Media Cybernetics, Silver Spring, Md.). The area of the whole specimen and the area of tissue penetration into the scaffold were measured. Another section was used to perform Factor VIII related antigen/von Willebrand factor immunohistochemical staining. Anti human Factor VIII related antigen/von Willebrand factor rabbit polyclonal antibody (NeoMarkers, Fremont, Calif.) and a DakoCytomation EnVision+® System-HRP (AEC) kit (Dako North America, Carpinteria, Calif.) were used. The area and number of positive stained blood vessels inside scaffolds were measured.

Results and Discussion

Tissue Regeneration in PDGF-NMS Containing Scaffolds In Vivo

Figure 7A:
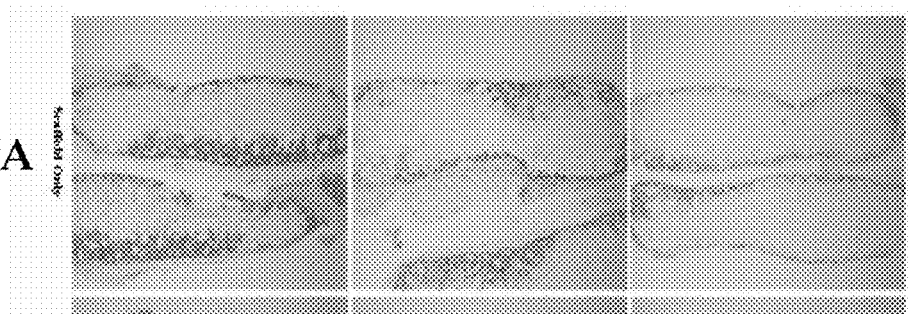
FIGS. 7A through 7I are cross sections through the diameters of circular shaped disks of scaffold specimens harvested at 7 days after subcutaneous implantation in a rat ectopic model (standard H & E staining with an original magnification of 2×); in each cross section in the respective Figures (which represents the same group of specimen) the neo tissue completely penetrated throughout the scaffolds in all groups with PDGF (platelet-derived growth factor)-containing NMS (nano- and micro-spheres) including both doses (2.5 µg PDGF and 25 µg PDGF) with both release rates (slow and fast) (FIGS. 7F-7I), the neo tissue penetrated partially into the scaffolds in groups without PDGF-containing NMS, including the scaffold alone (FIG. 7A), scaffold+empty slow NMS (FIG. 7B), scaffold+empty fast NMS (FIG. 7C), scaffold coated with 2.5 µg PDGF (FIG. 7D), and scaffold coated with 25 µg PDGF groups (FIG. 7E)
Figure 7B:
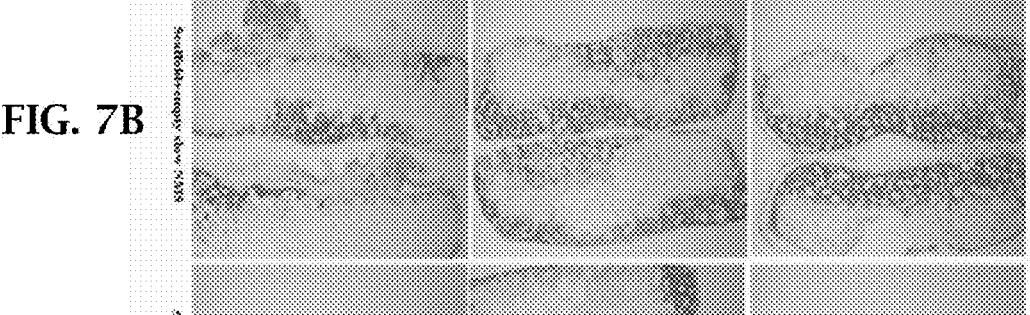
Figure 7C:
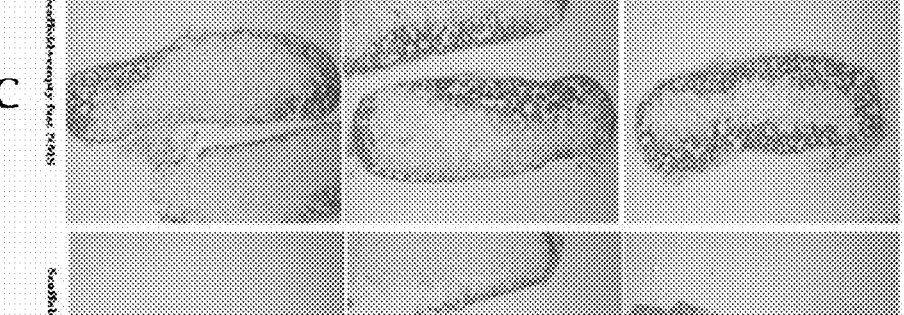
Figure 7D:
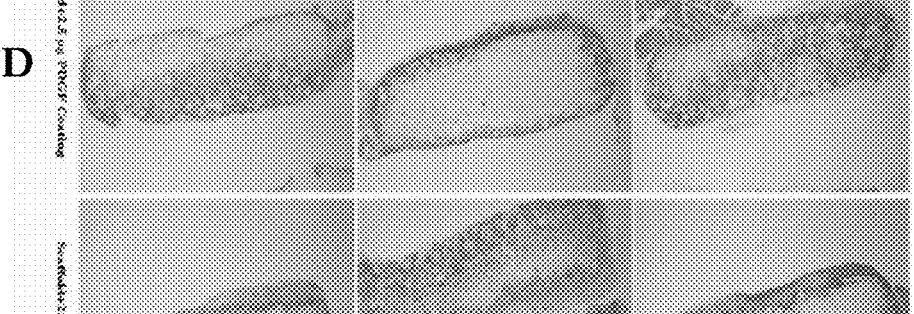
Figure 7E:
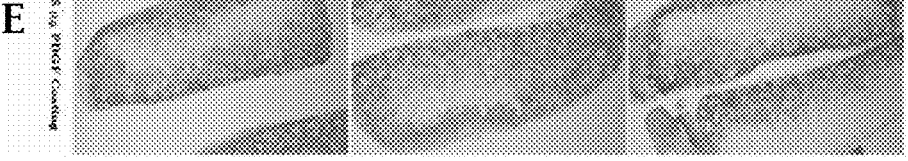
Figure 7F:
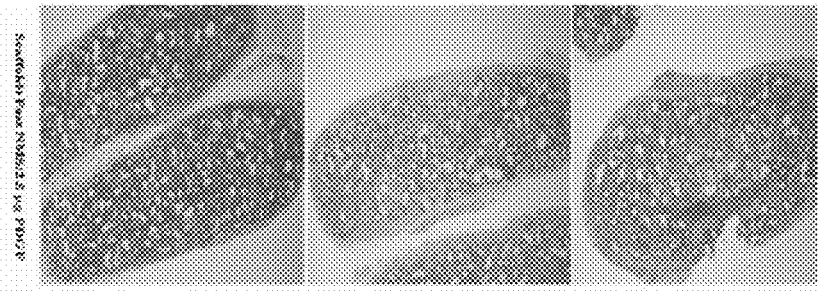
Figure 7G:
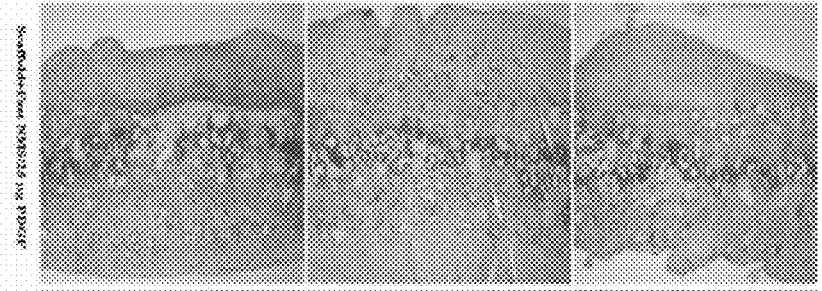
Figure 7H:
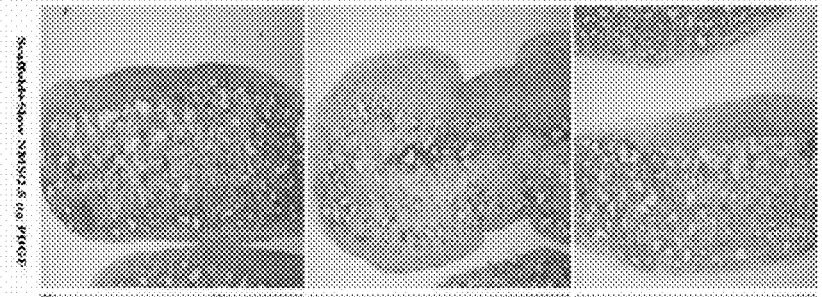
Figure 7I:
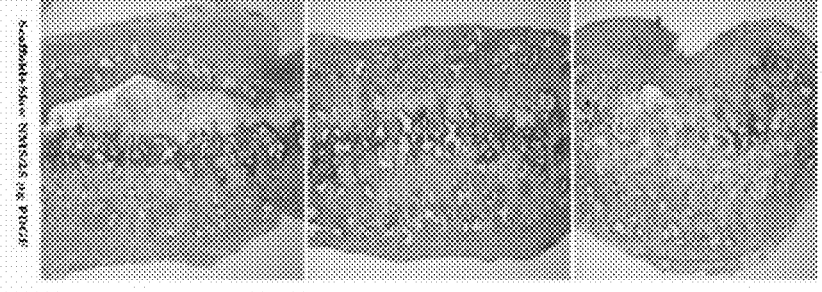

In the ectopic implantation model, the tissue neogenesis and penetration into the scaffolds were examined using standard H&E histological evaluation. At 3 days after implantation, no appreciable level of tissue ingrowth into scaffolds was found in all groups (data not shown). At 1 week, there were significant differences in tissue neogenesis among different groups (See FIGS. 1A through 1I). As depicted, there was minimal tissue neogenesis and penetration into the scaffold alone group (FIG. 7A), and the scaffold devoid of PDGF groups (containing empty NMS, FIGS. 7B and 7C). The scaffolds that were soaked with PDGF-BB (FIGS. 7D and 7E) did not show significantly better tissue neogenesis than the scaffold alone (FIG. 7A) or scaffold with empty NMS groups (FIGS. 7B and 7C). In contrast, complete tissue neogenesis was demonstrated in scaffolds with PDGF-NMS (FIGS. 7F through 7I). The scaffolds containing slower releasing PDGF-NMS (FIGS. 7H and 7I) had significantly more tissue neogenesis than the scaffolds with faster releasing PDGF-NMS (FIGS. 7F and 7G).

Figure 8A:
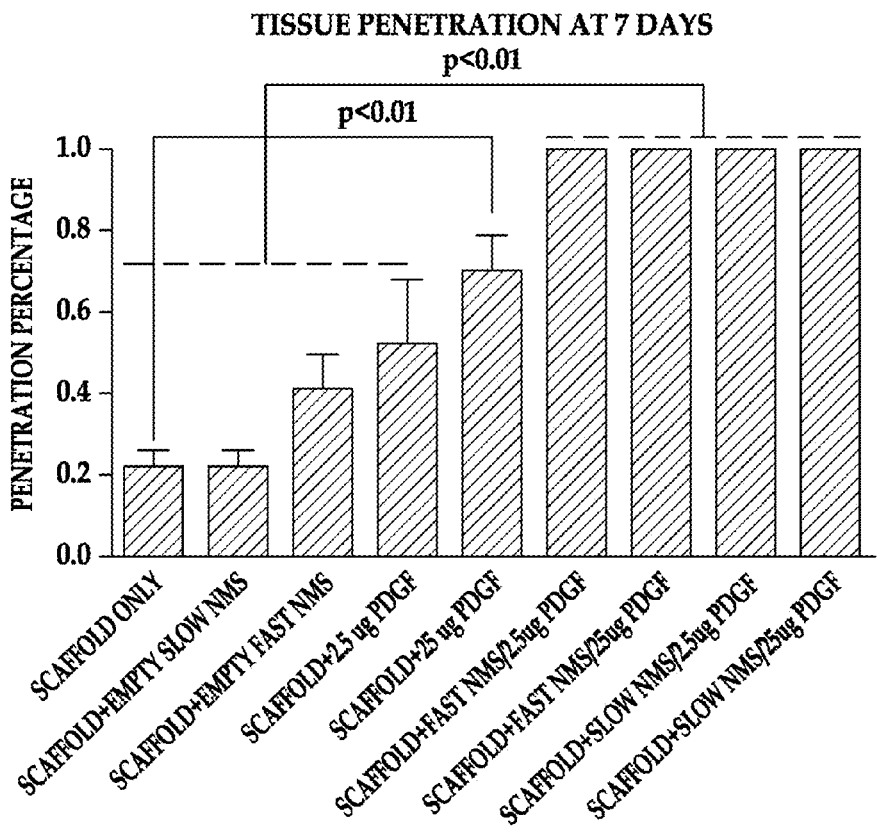
FIG. 8A is a graph depicting the percentage of penetrated tissue area (×10$^{-2}$) versus whole scaffold area (×10$^{-2}$) for the specimens harvested at 7 days after subcutaneous implantation in the rat ectopic model (shown in FIGS. 7A-7I)

The observations of tissue neogenesis shown in the FIG. 7 series were supported by quantification of the histological images (see FIG. 8A). In all scaffold groups that contained PDGF-NMS (FIGS. 7F through 7I), 100% tissue penetration was achieved. At low dose (2.5 µg PDGF), the PDGF coated scaffolds (FIG. 7D) did not result in significantly more tissue penetration over control groups (no PDGF, see FIGS. 7A through 7C). However, at high dose (25 µg), the PDGF coated scaffolds (FIG. 7E) resulted in statistically more tissue penetration over control groups. In addition, there were more vascularization and thicker connective tissue capsule surrounding scaffolds in the groups with PDGF-NMS than in the groups without PDGF-NMS.

Figure 8B:
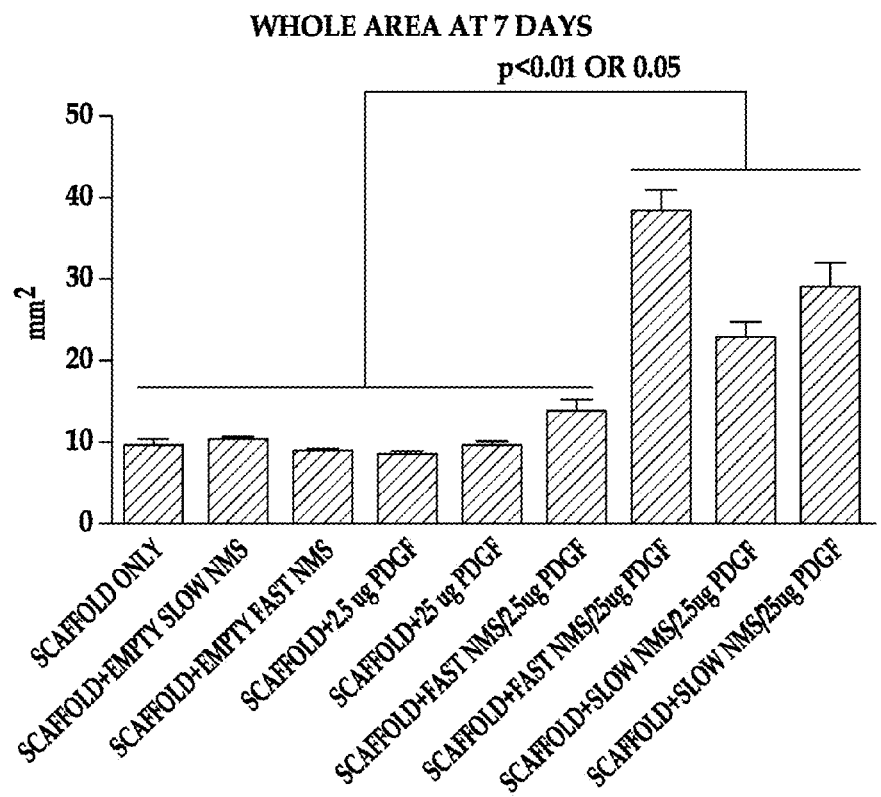
FIG. 8B is a graph depicting the total cross section areas (along the diameters of the disk specimens) of neo tissue for the specimens harvested at 7 days after subcutaneous implantation in the rat ectopic model (shown in FIGS. 7A-7I)

Perhaps the most prominent manifestation in the groups with PDGF-NMS was that due, at least in part, to the strong tissue growth inside the scaffolds, the scaffolds become larger in volume and lost original shape, but also the porous structure of scaffolds appeared irregular and broken, relative to the groups without PDGF-NMS. At both high and low doses of PDGF, the slow releasing NMS resulted in significantly larger size of neo tissue formation, while only the high dose of PDGF in fast releasing NMS resulted in the significantly larger size of neo tissue formation (see FIG. 8B), demonstrating the advantages of slow releasing PDGF-NMS in the scaffolds. At 2 and 3 weeks, the ingrowth tissue penetrated into the entire scaffolds in all groups (data not shown).

Angiogenesis in PDGF-NMS Containing Scaffolds

PDGF has been reported to promote blood vessel formation. In order to explore the in vivo biological functions of PDGF delivered by NMS in nanofibrous scaffolds, the vascularization in scaffolds was investigated using Factor VIII staining and hematoxylin counterstaining. At 3 days after implantation, there was no appreciable level of angiogenesis in any scaffold group (data not shown). FIGS. 9A through 9E depict PDGF-NMS scaffolds (FIGS. 9A though 9D) and one control (FIG. 9E) one week after the implantation. These results indicate that the level of angiogenesis is dependent on the PDGF dose. In the control group (scaffold alone, FIG. 9E), there was minimal new blood vessel formation and tissue penetration into the scaffolds. In the scaffolds containing PDGF-NMS, there was appreciable new blood vessel formation, increasing with increased PDGF dose (compare FIG. 9A with FIG. 9B, and compare FIG. 9C with FIG. 9D). The angiogenesis is also dependent on the rate of PDGF release from the NMS. At the same dose, the slow releasing NMS groups showed more blood vessel formation than the fast releasing NMS groups (compare FIG. 9A with FIG. 9C, and compare FIG. 9B with FIG. 9D).

Figure 10A:
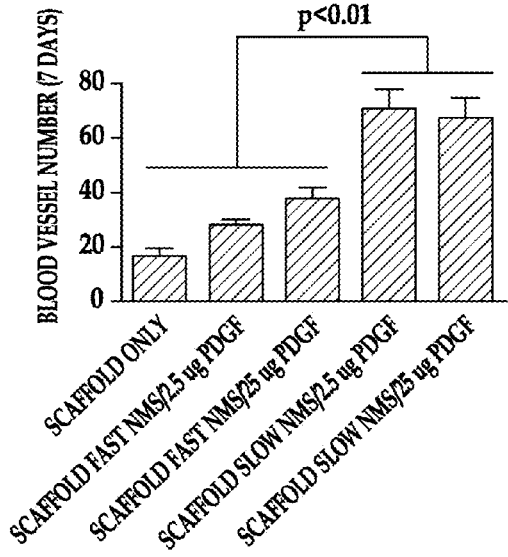
FIGS. 10A and 10B are graphs depicting the quantification of newly formed blood vessels in number (FIG. 10A) and total area (FIG. 10B) from the histological images shown in FIGS. 9A through 9E, each data point is calculated from 5 randomly selected fields of the specimens harvested at 7 days after implantation in the rat ectopic model.
Figure 10B:
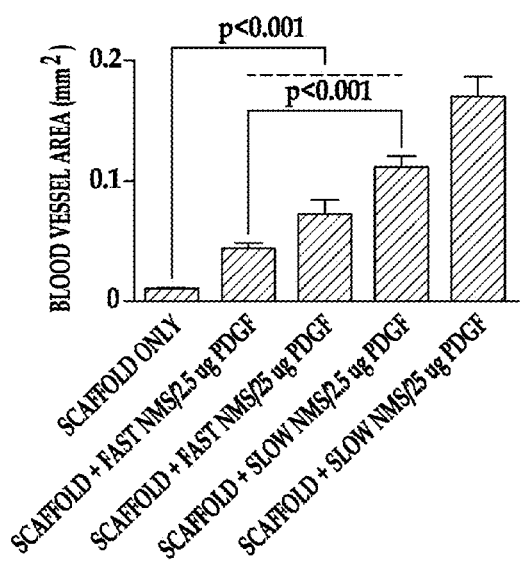

These results were confirmed by quantifying the numbers (see FIG. 10A) and areas (see FIG. 10B) of the blood vessels in these scaffolds. At 2 and 3 weeks, the differences in blood vessel number among all the scaffold groups were not statistically significant (data not shown).

The data disclosed herein demonstrates that the PDGF released from NMS in the nano-fibrous scaffolds remains angiogenic, chemotaxic, and/or mitogenic in vivo. It is believed that the biodegradable polymer NMS maintains the integrity of the PDGF-BB molecules, such that the molecules retain their biological activity. Both tissue regeneration and angiogenesis can advantageously be achieved in scaffolds containing PDGF NMS.

Example 3

Polymeric Microsphere (MS) Preparation

Poly(lactide-co-glycolide) microspheres having a diameter in the sub-micrometer to nanometer range were fabricated using a double emulsion technique. 100 µl of a 3 mg/ml PDGF-BB solution (in 20 mM sodium acetate, pH=6.3) were emulsified into 1 ml of 10% PLGA with molecular weight of 6.4 kD or 65 kD in dichloromethane (DCM) solution, using a probe sonicator at 15 W (Virsonic 100, Cardiner, N.Y.) for 10 seconds over an ice bath to form the primary water-in-oil (w/o) emulsion. The w/o emulsion was then mixed with 20 mL of 1% PVA aqueous solution under sonication to form a water-in-oil-in-water (w/o/w) double emulsion. The double emulsion was magnetically stirred at room temperature (RT) for at least 3 hours to evaporate dichloromethane, and then was centrifuged to collect the solid microspheres. The resultant microspheres containing PDGF-BB were washed twice with distilled water, freeze-dried, and stored at −80° C. until use.

Fabrication of Poly(L-Lactic Acid) (PLLA) Nanofibrous Scaffolds

PLLA macroporous nano-fibrous scaffolds were fabricated using phase separation and sugar-leaching techniques. 600 µl of 10% PLLA/THF solution were cast under mild vacuum into an assembled sugar template by bound sugar spheres approximately 250-425 µm in diameter. The polymer/sugar composite was phase separated overnight at −20° C. and then immersed for 2 days in cyclohexane to exchange THF. Following lyophilization, the sugar spheres were leached out in distilled water and highly porous scaffolds were formed. After re-lyophilizing, the scaffolds were cut into circular disks with dimensions of 7.2 mm in diameter and 2 mm in thickness. The average weight of the porous scaffolds ranged from about 2.5 mg to about 3.0 mg each.

Incorporation of PLGA Microspheres into PLLA

The PLGA microspheres containing PDGF-BB were incorporated into PLLA nano-fibrous scaffolds using a post-seeding method. Dry PLGA microspheres were suspended in hexane at a concentration of 5 mg MS/ml. 80 µL of the suspension were seeded onto each scaffold, and the scaffold was air-dried for 30 minutes to evaporate the solvent. This procedure was repeated until one scaffold contained 2.5 µg and 25 µg rhPDGF-BB, respectively (BioMimetic Therapeutics, Inc., Franklin, Tenn.). This calculation was based on a 77% encapsulation efficiency of PDGF-BB in the microspheres. The scaffolds were then subjected to a mixed solvent of hexane/THF (volume ratio of 90/10) to immobilize the microspheres on the scaffolds, which were then vacuum-dried for 3 days to remove the solvent. The controls were scaffolds seeded with microspheres that did not include PDGF-BB.

PDGF Scaffold Implantation In Vivo

To investigate the effect of PDGF release rate on PDGF biological function in vivo, nine groups of 3 animals each were prepared to test in a rat wound healing model. Table 2 illustrates the grouping of the animals.

TABLE 2

Example 3 Scaffolds implanted in vivo

| Group | Scaffold | Coating |
|---|---|---|
| A | Nanofibrous scaffold | None |
| B | Nanofibrous scaffold | 65 kD microspheres without PDGF-BB |
| C | Nanofibrous scaffold | 6.4 kD microspheres without PDGF-BB |
| D | Nanofibrous scaffold | 2.5 µg PDGF-BB (simple coating) |
| E | Nanofibrous scaffold | 25 µg PDGF-BB (simple coating) |
| F | Nanofibrous scaffold | 6.4 kD microspheres containing 2.5 µg PDGF-BB |
| G | Nanofibrous scaffold | 6.4 kD microspheres containing 25 µg PDGF-BB |
| H | Nanofibrous scaffold | 65 kD microspheres containing 2.5 µg PDGF-BB |
| I | Nanofibrous scaffold | 65 kD microspheres containing 25 µg PDGF-BB |

Under isoflurane anesthesia, mid-sagittal incisions were made on the dorsa of Sprague Dawley rats (200 g weight). Each scaffold implant construct was inserted into a surgical pocket in triplicate for each assay (using 3 different rats). The incisions were stapled shut. Assays included histologic analysis (n=3 animals/group) and cDNA Array/real time PCR analysis (n=3 animals/group). Four blocks were placed in each animal, and the implants were harvested at 3, 7, 14, and 21 days.

Histology, Histomorphometry and Immunohistochemistry

The harvested pellets were fixed in 10% neutral buffered formalin, embedded in paraffin, and longitudinally cut into 4 or 5 µm thick cross sections. Selected sections were stained with hematoxylin and eosin (H&E) to evaluate the nature of tissue neogenesis. Images of these specimens were captured using a Nikon Eclipse 50i microscope (Nikon, Inc., Melville, N.Y.) fitted with a Nikon Digital Sight DS U1 camera (Nikon, Inc., Melville, N.Y.) for analysis using Image Pro Plus™ software (Media Cybernetics, Silver Spring, Md.). The entire area of the specimen and the area of tissue penetrating into the scaffolds were measured. The remaining slides were used to perform Factor VIII-related antigen/von Willebrand factor immunohistochemical staining with an anti-human Factor VIII-related antigen/von Willebrand factor rabbit polyclonal antibody (NeoMarkers, Fremont, Calif.) and a DakoCytomation EnVision+® System-HRP(AEC) kit (Dako North America, Carpinteria, Calif.). The area and number of positive-stained blood vessels inside the scaffolds were measured.

RNA Extraction and Purification

After removal of the tissue-scaffold implants, pellets were placed into liquid nitrogen, pulverized into fine particles, and transferred into 15 mL centrifuge tubes. Total RNA extraction was performed using TRIzol® reagent (Invitrogen, Carlsbad, Calif.) according to the manufacturer's protocol. About 2 mL TRIzol® was added into each tube, and the tubes were placed at room temperature for about 20 minutes. After centrifugation at 3000 rpm for 15 minutes, the supernatants were transferred into new tubes. Following protein denaturation by chloroform addition and centrifugation, RNA was precipitated by isopropanol, washed with 75% alcohol and dried. The RNA was then solubilzed and cleaned using DNase I and the RNeasy Mini Kit (QIAGEN Inc, Valencia, Calif.) according to provided protocols.

Affymetrix GeneChip Analysis

Figure 12A:
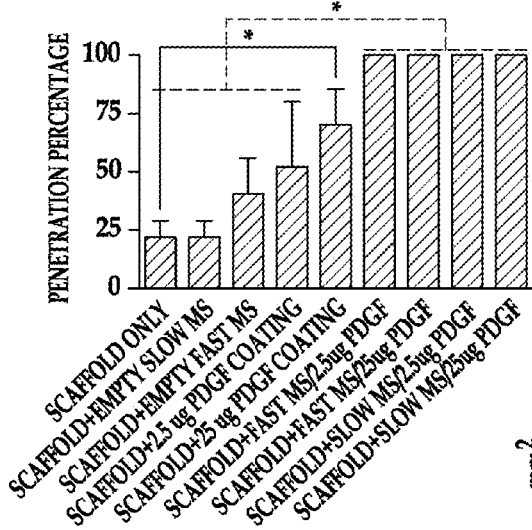
FIGS. 12A and 12B are graphs depicting the histomorphometric analysis results of PDGF-inducing tissue penetration and neogenesis, where FIG. 12 A is the percentage of tissue penetration for each of the listed samples and * represents statistically significant differences p<0.01 and FIG. 12B demonstrates the area of tissue penetration for each of the listed samples and ** represents statistically significant differences p<0.05.
Figure 12B:
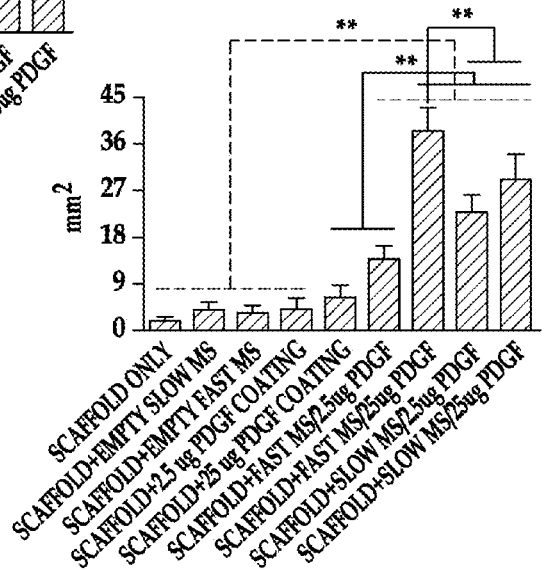
Figures 11A, 11B, 11C, 11D, 11E, 11F:
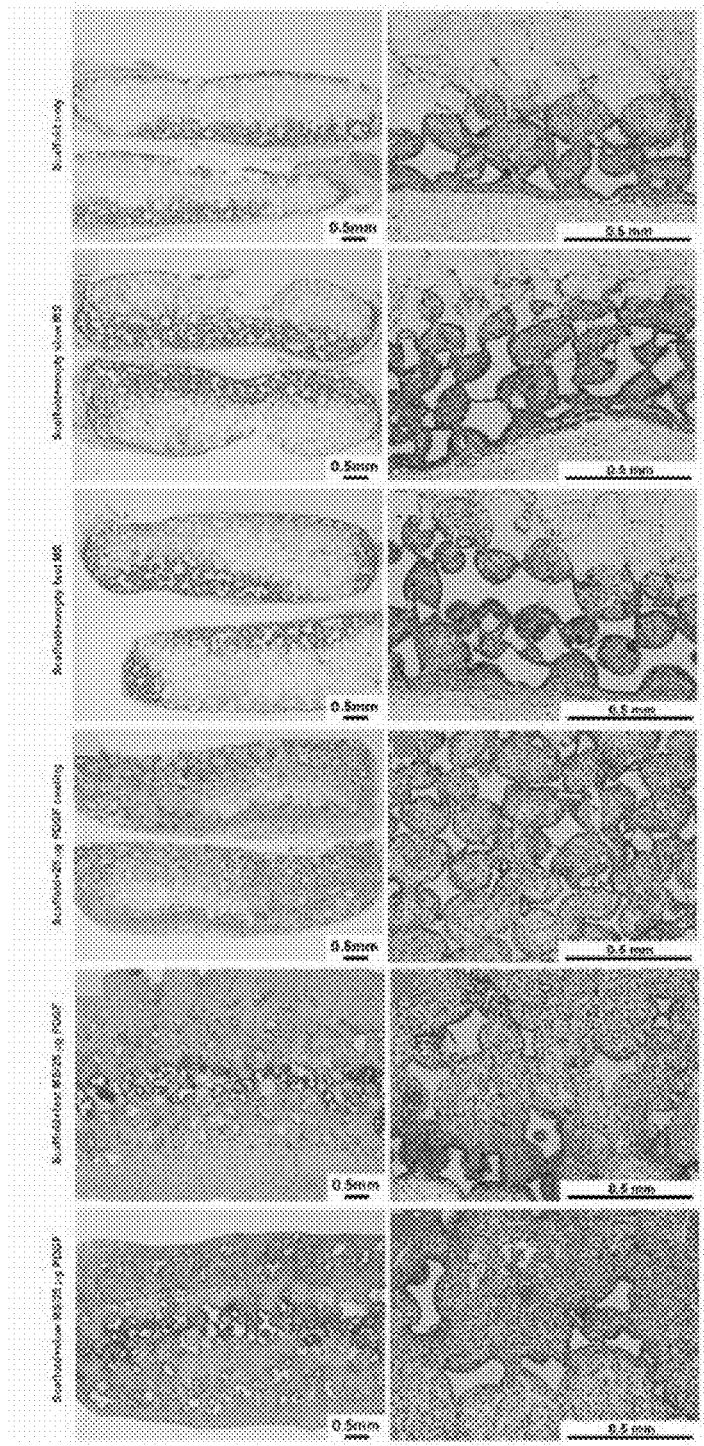
FIGS. 11A through 11F are cross sections through the diameter of circular shaped disks of scaffold specimens harvested at 7 days after subcutaneous implantation in a rat (standard H & E staining with an original magnification of 2× (left image in FIGS. 11A through 11F) and higher magnification of 10× (right image in FIGS. 11A through 11F))

From histology, the groups of nanofibrous scaffolds carrying 25 μg PDGF in microspheres had the most obvious tissue penetrations and tissue neogenesis (see FIGS. 12A and 12B). Thus, in order to screen the potential genes related to PDGF function in vivo, those two groups (groups G and I) were selected. 5 μg RNA from each of 3 specimens in each group was pooled together as the sample for Affymetrix GeneChip Analysis to screen for potential gene candidates to be subsequently assessed by quantitative real-time PCR. The group of empty nanofibrous scaffolds (group A) was used as a control.

10 μg of total RNA was quantitatively amplified and biotin-labeled according to the Affymetrix GeneChip Expression Analysis Technical Manual. RNA was converted to double-stranded complementary DNA (cDNA) using a SuperScript II RT kit (Invitrogen, Carlsbad, Calif.) with a $T_7$-$T_{24}$ primer (Proligo). The cDNA was then used for in vitro transcription in the presence of biotin-modified ribonucleotides (Enzo) to amplify single-stranded RNA. The biotin-labeled RNA was fragmented and 10 mg hybridized to a gene chip (Rat Genome 230 2.0 Array (Affymetrix, Santa Clara, Calif.)) at 45° C. for about 16 hours. Chips were washed and stained with streptavidin R-phycoerythrin (Molecular Probes). After scanning the chips, the data were analyzed using Affymetrix GeneChip related software, Microarray Suite and Data Mining Tool.

Quantitative Real-Time PCR

To verify the cDNArray results, quantitative Real-time PCR was performed using ABI Prism Sequence Detection System 7700 (Applied Biosystems, Foster City, Calif.). First, 1 mg total RNA was used as a template to generate cDNA with an oligo d(T) primer using the TaqMan Reverse Transcription Reagents kit (Applied Biosystems, Foster City, Calif.). Thermal conditions were: 25° C., 10 minutes; 48° C., 30 minutes; and 95° C., 5 minutes. For the real time PCR, a 30 ml PCR reaction was prepared with 1 mL cDNA (RT product) and 1.5 mL mixture of gene specific probe (FAM dye) and primers from Applied Biosystems. The sequences for the probes are listed in Table 3. The PCR thermal conditions were: 50° C., 2 minutes; 95° C., 10 minutes; followed by 40 cycles of 95° C., 15 seconds and 60° C., 1 minutes. The ABI Prism Sequence Detection System 7700 and its operational software are capable of determining the linear phase of PCR reaction. An 18S primer and probe was used as an endogenous control.

TABLE 3

Real-time PCR probe sequences

| Genes | Probe Sequence |
|---|---|
| CXCL1 | TTGTCCAAAAGATGCTAAAGGGTGT (SEQ ID NO 1) |
| CXCL2 | TCCAAAAGATACTGAACAAAGGCAA (SEQ ID NO 2) |
| CXCL5 | GAGCTCAAGCTGCTCCTTTCTCGGC (SEQ ID NO 3) |
| CCL21b | GCTCCAAAGGCTGCAAGGGGACTGA (SEQ ID NO 4) |

Statistics Analysis

The differences among groups for tissue penetration, tissue area, blood vessel number and gene expressions in real time PCR were statistically assessed by one-way analysis of variation (ANOVA) with Tukey multiple comparison post hoc test using a statistical software package Prism 4 (GraphPad Co. San Diego, Calif.). Each group had 3 samples. The level of significance was set as $p<0.05$. Results demonstrating statistically significant differences and an arbitrary 10-fold cut-off for change were subsequently considered for quantitative real time PCR analysis.

Results

Histology and Histomorphometry

At 3 days post-implantation, no significant tissue ingrowth into the scaffolds was found in any of the groups (data not shown). However, at 1 week, penetrating tissue occupied the entire scaffold spaces in several groups carrying PDGF encapsulated in microspheres (F, G, H and I), while the tissue penetration was seen in the superficial regions of scaffolds in the groups (D and E) with simply coated PDGF and the groups without PDGF (A, B, and C) (see FIGS. 11A through 11F).

In addition, there was more vascularization and thicker connective tissue capsules surrounding scaffolds in the groups with PDGF encapsulation by microspheres (groups F, G, H and I) than without PDGF containing microspheres (groups A, B, C, D and E). The scaffolds in the groups with PDGF encapsulation by microspheres became larger in volume than their original shape and the porous structure also appeared irregular and distorted. This is in contrast to the groups without PDGF encapsulated by microspheres. In particular, these findings were more noticeable in the groups of scaffolds with high dose PDGF microspheres than with low dose PDGF microspheres. At 2 and 3 weeks, tissue invaded into the entire scaffold area for all groups (data not shown).

In parallel with the 1 week histological observations, the histomorphometry measurement results of 1 week specimens (see FIG. 12B) showed that the areas representing the specimen volume were significantly greater in the G, H, and I groups than the other groups. With regard to the tissue penetration percentage (see FIG. 12A) (penetration tissue area versus the whole area), the tissue penetration in the groups containing PDGF encapsulated by microspheres (groups F, G, H and I) was greater than groups A, B, C, and D.

The percentage (see FIG. 12A) of tissue penetration within the groups of PDGF encapsulated in PLGA microspheres (groups F, G, H, I) was statistically greater than that for the other groups, with the exception of the 25 μg PDGF coating group (group E). The percentage of tissue penetration in the 25 μg PDGF coating group is significantly greater than for the scaffold only group (group A).

The areas (see FIG. 12B) in the groups of PDGF encapsulated in PLGA microspheres (groups F, G, H, I) are statistically larger than those in the groups for scaffold only (group A), scaffolds containing empty slow and fast release PLGA microspheres (groups B and C), and scaffold with 2.5 μg PDGF coating (group D). The group with 2.5 μg PDGF encapsulated in slow release PLGA microspheres (group H) and 25 μg PDGF encapsulated in slow and fast release PLGA microspheres (groups I and G) have larger areas than the group with 25 μg PDGF coating and 2.5 μg PDGF encapsulated in fast release PLGA microspheres (groups E and H). The largest area was found in the group having 25 μg PDGF encapsulated in fast release PLGA microspheres (group G).

PDGF-BB MS in NFS Stimulates Neovascularization In Vivo

Figure 13A:
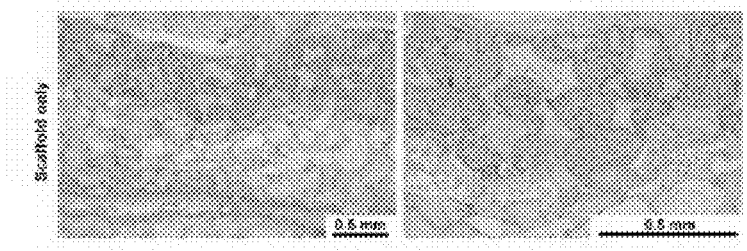
FIGS. 13A through 13C are cross sections through the diameter of circular shaped disks of scaffold specimens harvested at 7 days after subcutaneous implantation in a rat (Positive Factor VIII staining with an original magnification of 10× (left image in FIGS. 13A through 13C) and higher magnification of 40× (right image in FIGS. 13A through 13C)), all of the Figures show that blood vessels were located in the central regions of the pores within penetrated tissues, and that blood vessels also crawled through the inter-openings between each pore, however, the groups with 25 µg PDGF encapsulated in fast and slow release PLGA microspheres (FIGS. 13B and 13C, respectively) had measurably more vascularization than the group with no PDGF (FIG. 13A)
Figure 13B:
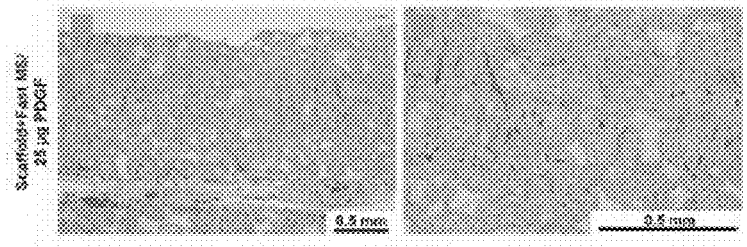
Figure 13C:
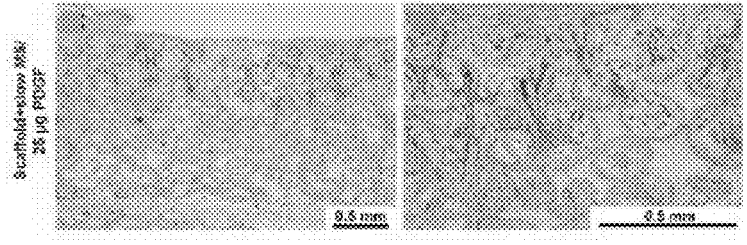

In order to explore the in vivo biological functions of PDGF delivered by microspheres in nanofibrous scaffolds on blood vessel formation, the vascularization within the scaffolds was investigated using Factor VIII-related antigen/von Willebrand factor immunohistochemical staining. FIGS. 13A (group A), 13B (group G) and 13C (group I) indicate that at 7 days, vascularization formed inside scaffolds was greater in groups G, H (not shown) and I, which is in accordance with the results of measurements of blood vessel number.

Figure 14:
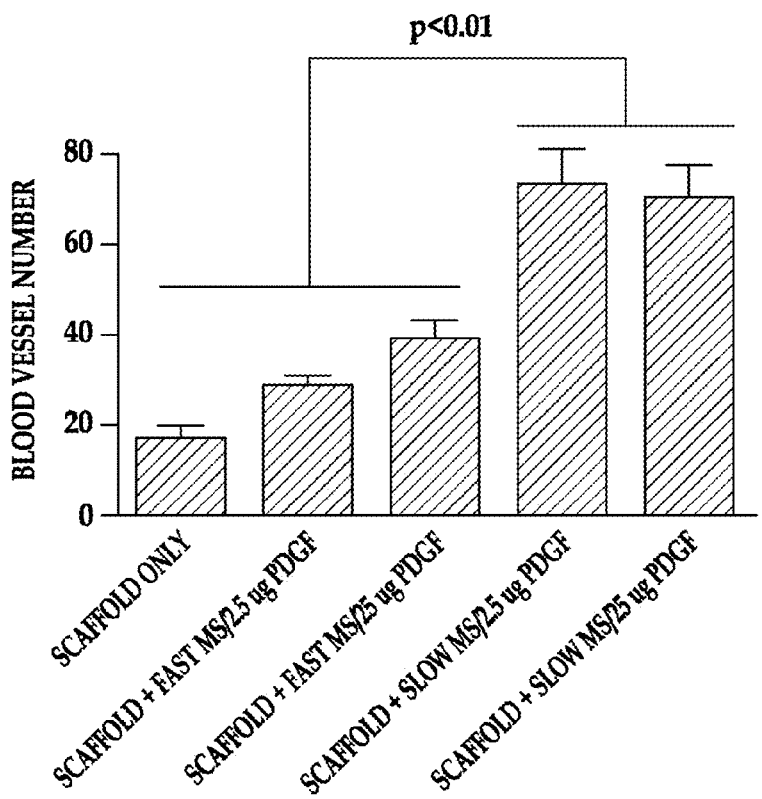
FIG. 14 is a graph depicting that PDGF-containing microspheres in nanofibrous scaffolds increases angiogenesis in vivo, where p<0.01.

There were significantly more blood vessels formed in groups H and I, which contained PDGF encapsulated in high molecular weight microspheres (see FIG. 14). The blood vessel number was measured within each group using sections immunostained with Factor VIII antibody. The blood vessel number of PDGF-encapsulated in the fast release PLGA group showed very little difference from that in the scaffold-only group. At 3, 14, and 21 days, blood vessel number in the scaffolds displayed no significant difference among all groups (data not shown).

cDNA Array Screening for Potential PDGF-Inducible Genes

In order to screen the potential gene expression changes induced by PDGF, RNA was extracted from 7 day old specimens and used to perform cDNA array analysis. In order to target genes more sensitive to PDGF's effects, a 10-fold change in gene expression was used as the cut-off, and the results are displayed in Table 4. The cDNA array profiles demonstrate that PDGF primarily up-regulated the expression of three groups of potential genes. First, chemokine family genes such as CXCL1, 2, 5, and CCL 21b were up-regulated ranging from 48.4-fold to 148.9-fold. However, CCL22 was down-regulated by 15.6-fold. Secondly, muscle-related or cell-backbone-related genes such as (x-actin, myosin, and tropomyosin were increased ranging from 10.2-fold to 117-fold. Thirdly, interleukin-1 (IL-1) related genes such as IL-1 alpha, beta, and IL-1 receptor were up-regulated by 12-15-fold. Cystatin E/M and carboxylesterase 3 were most prone to down-regulation by PDGF. The gene expression changes of chemokine and IL-1 family were confirmed by quantitative real-time PCR (FIGS. 15A through 15D and FIGS. 16A through 16D).

TABLE 4

10-fold Change in Gene Expression

| Genes | Fold Change |
| --- | --- |
| chemokine (C—X—C motif) ligand 1 | 148.95 |
| actin, alpha 1, skeletal muscle | 117.12 |
| myosin, light polypeptide 2 | 86.93 |
| similar to stefin A2 (predicted) | 83.67 |
| chemokine (C—X—C motif) ligand 5 | 66.65 |
| chemokine (C—X—C motif) ligand 2 | 63.04 |
| chemokine (C-C motif) ligand 21b (serine) | 48.4 |
| matrix metallopeptidase 3 | 47.66 |
| Tryptophan hydroxylase 1 | 35.83 |
| Transcribed locus | 29.88 |
| S100 calcium binding protein A9 (calgranulin B) | 28.19 |
| S100 calcium binding protein A8 (calgranulin A) | 26.65 |
| colony stimulating factor 3 (granulocyte) | 26.22 |
| gene model 1960, (NCBI) | 25.67 |
| similar to RIKEN cDNA 4933425K02 (predicted) | 25.21 |
| 1388204_at | 24.11 |
| similar to MGC15476 protein (predicted) | 23.44 |
| sortilin-related receptor, L(DLR class) A repeats-containing (predicted) | 21.17 |
| Tropomyosin 1, alpha | 21.12 |
| EGF-like-domain, multiple 6 | 20.42 |
| carbonic anhydrase 4 | 19.61 |
| Transcribed locus, moderately similar to XP_574280.1 PREDICTED: similar to Ab2-143 | 19.08 |
| Transcribed locus, moderately similar to XP_574280.1 PREDICTED: similar to Ab2-143 | 19.06 |
| fast myosin alkali light chain | 18.88 |

TABLE 4-continued 10-fold Change in Gene Expression

| Genes | Fold Change |
| --- | --- |
| gene model 1960, (NCBI) | 18.66 |
| inhibin beta-A | 17.59 |
| interleukin 1 beta | 15.24 |
| neurotrophin receptor associated death domain | 15.07 |
| myoglobin | 14.64 |
| interleukin 1 receptor, type II | 13.96 |
| Transcribed locus | 13.59 |
| gene model 1960, (NCBI) | 13.24 |
| Transcribed locus | 13.07 |
| interleukin 1 alpha | 12.83 |
| Transcribed locus | 11.94 |
| ephrin A1 | 11.81 |
| Transcribed locus | 11.25 |
| cAMP responsive element modulator | 10.57 |
| procollagen, type XI, alpha 1 | 10.57 |
| 1392736_at | 10.55 |
| breast cancer anti-estrogen resistance 1 | 10.38 |
| galanin | 10.2 |
| myosin, heavy polypeptide 4, skeletal muscle | 10.17 |
| prokineticin 2 | 10.13 |
| 1385589_at | 10.08 |
| Down-regulated | |
| cystatin E/M | −50.08 |
| carboxylesterase 3 | −29.99 |
| 1375077_at | −20.03 |
| elastase 1, pancreatic | −18.79 |
| Similar to PIRB1 (predicted) | −17.71 |
| CD5 antigen-like | −17.63 |
| chemokine (C—C motif) ligand 22 | −15.63 |
| secretin receptor | −14.91 |
| Similar to Ifi204 protein (predicted) | −10.96 |
| thyroid hormone responsive protein | −10.77 |

Real-Time PCR Confirmation of PDGF-BB Induction

Figure 15A:
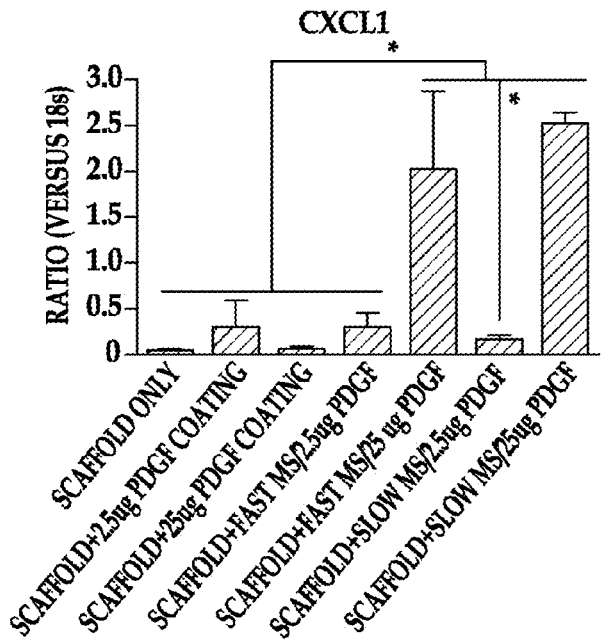

Since most gene expression changes were found in chemokine family genes from the cDNArray profile, Real time PCR was used to investigate these genes in more detail. As shown in FIGS. 15A and 15B, CXCL1 gene expression was higher in groups containing 25 µg PDGF encapsulated in high and low molecular weight PLGA microspheres than in other groups, while higher CXCL2 gene expression was found in the group containing 25 µg PDGF encapsulated in high molecular weight PLGA microspheres, compared to all other groups. In addition, CXCL5 gene expression (see FIG. 15C) in the groups containing 25 µg PDGF encapsulated in PLGA microspheres was higher than that of the scaffold alone group and the two groups of scaffolds with PDGF coatings. Furthermore, the group containing 25 µg PDGF encapsulated in high molecular weight PLGA microspheres also had more CXCL5 gene expression, compared to 2.5 µg PDGF encapsulated in the low molecular weight PLGA microspheres group. With regard to the CCL21b gene (see FIG. 15D), the scaffold with 25 µg PDGF encapsulated in high molecular weight PLGA microspheres had stronger CCL21b transcription than the scaffold alone and both scaffolds including PDGF coatings. The CCL21b gene expression within the group containing 25 µg PDGF encapsulated in low molecular weight PLGA microspheres was higher compared to the scaffold alone group, the two groups of scaffolds having PDGF coatings, and the 2.5 µg PDGF encapsulated in low molecular weight PLGA microspheres group. There was no statistically significant difference between high and low molecular weight microspheres groups containing either 25 µg PDGF or 2.5 µg PDGF.

Discussion

The results of Example 3 show that a PLLA nanofibrous scaffold/PLGA microsphere construct is favorable for PDGF delivery in vivo and promotes tissue neogenesis and vascularization. Furthermore, such in vivo PDGF functions have a close relationship with chemokine family members CXCL1, 2, 5, and CCL 21b and 22. Among them, CXCL1 has been shown to be a PDGF-induced early gene.

It has been shown that in vitro release rate of PDGF encapsulated in PLGA microspheres can be controlled by PLGA molecular weight. High molecular weight PLGA microspheres containing PDGF generally take a longer time to be degraded (than low molecular weight PLGA) and consequently release PDGF more slowly, and vice versa. Example 3 illustrates that PLGA molecular weight has a relationship to the in vivo effects of PDGF encapsulated by PLGA on tissue neogenesis and vascularization. The groups with PDGF encapsulated in PLGA microspheres had 100% tissue penetration, while the groups with PDGF coated on the surface of PLLA nanofibrous scaffolds resulted in 20%-75% tissue penetration. Furthermore, specimen areas in the groups with 25 μg PDGF encapsulated in low and high molecular weight PLGA microspheres and 2.5 μg PDGF encapsulated in high molecular weight PLGA microspheres were much larger than other groups. These results indicate that tissue penetration and specimen area are dependent on in vivo PDGF release rate. In addition, the results of blood vessel number and area also shown to have a similar relationship with in vivo PDGF release.

The effects of delivery systems on in vivo PDGF function were explored at the molecular level. The family of chemokines is composed of small molecular weight peptides with highly conserved cysteine motifs. Members of the chemokine family are categorized into four groups, depending on the spacing of their first two cysteine residues. Certain inflammatory chemokines activate cells to initiate an immune response or promote wound healing. CXC chemokines have two N-terminal cysteines, separated by one amino acid, and are subdivided into two groups, those with a specific amino acid motif of Glutamate-Leucine-Arginine (ELR) immediately before the first cysteine of the CXC motif (ELR-positive), and those without an ELR motif (ELR-negative). ELR-positive CXC chemokines specifically induce the migration of neutrophils, and interact with chemokine receptors CXCR1 and CXCR2. It is believed that such processes link PDGF's effects during the inflammatory cascade associated with subsequent tissue neogenesis.

Chemokine gene expression may be stimulated by many factors, including growth factors such as PDGF and proinflammatory cytokines such as TNFα and IL-1. These growth factor- and cytokine-initiated chemokine gene expression effects occur primarily through a phosphatidylinositol 3 kinase (PI3k)-Akt-Ikk-NF-κB pathway. After NF-κB is activated, NF-κB moves to the cell nucleus and controls the expression of numerous genes related to inflammation, tumor development, immune responses and tissue repair. It has been shown that the human CXCL1 gene has an NF-κB binding site (GGGAATTTCC (SEQ ID NO 5)) in its upstream promoter region, which is essential for IL-1 to induce CXCL1 promoter activity. Therefore, the effects of PDGF on stimulating chemokine expression may depend on NF-κB.

In Example 3, PDGF induced chemokine gene expression in both dose-dependent and duration-dependent manners. The CXCL1 gene expression induced by 25 μg PDGF encapsulated in low and high molecular weight PLGA microspheres was higher than that in the scaffold alone group, the PDGF coating groups, and the low dose PDGF microsphere group. In contrast, CXCL1 gene expression induced by 2.5 μg PDGF encapsulated in low and high molecular weight PLGA microspheres had no significant differences from either the scaffold alone or PDGF coating groups, which indicates upregulation of CXCL1 gene expression stimulated by PDGF is dependent on PDGF dose. This relationship is also seen in chemokines CXCL2, CXCL5, and CCL21b.

However, the gene expression of CXCL1, 2, 5, and CCL21b induced by 25 μg PDGF coated on PLLA scaffolds (not encapsulated in PLGA microspheres) was not different from that by the empty scaffolds or 2.5 μg (low dose) PDGF microsphere groups, which suggests that PDGF release from PDGF-coated scaffolds may be too rapid to be effective. Thus, controlled delivery may be important for successful in vivo results.

Although PDGF induced expression of CXCL1, 2, and 5, the effects of these chemokines on PDGF function in vivo are still unclear. These chemokines seem not to influence PDGF functions on cell migration and proliferation, in part because there is reportedly no CXC receptor II (CXCR2) for CXCL1, 2 and 5 in normal human skin; however, CXCR2 has been found to be rich within endothelial cells, indicating these PDGF-inducible chemokines in Example 3 play a role in angiogenesis. In addition, CXCR2 is demonstrated to be the receptor responsible for ELR(+) CXC chemokine-mediated angiogenesis. (ELR motif: glutamate-leucine-arginine motif) PDGF and CXC chemokines may have synergistic effects on angiogenesis, in part because the PDGF effects focus on pericytes and vascular smooth muscle cells and improve blood vessel growth, while ELR(+) CXC chemokine primarily affects endothelial cells.

It is believed and Example 3 shows that a sustained release delivery system is key for in vivo PDGF application to promote tissue repair. In vivo, PDGF functions in a dose-dependent and release mode-dependent manner. A sustained release of PDGF not only influences tissue neogenesis and neovascularization, but also impacts the PDGF-induced gene profile of chemokine family members, actin, and interleukins. In addition, the chemokine family may be an important downstream factor for PDGF function. The use of controlled release nano-fibrous scaffolds incorporating PDGF-BB encapsulated microspheres offers significant potential for soft and hard tissue engineering applications.

The embodiments disclosed herein are effective for controlling the delivery of biomolecules and bioactive factors from a 3D porous scaffold. It is believed that the porous objects and methods are versatile, and may be used with a variety of proteins, growth factors, cytokines and bioactive molecules. The combination of controlled delivery and 3D biomimetic scaffold design provides an advantageous system for tissue engineering.

While several embodiments have been described in detail, it will be apparent to those skilled in the art that the disclosed embodiments may be modified. Therefore, the foregoing description is to be considered exemplary rather than limiting.

What is claimed is:

1. A porous object, comprising:
a polymer scaffold having nano-fibrous walls, internal pore surfaces and external pore surfaces; and
releasing material encapsulated biomolecules immobilized on at least one of the internal pore surfaces, the external pore surfaces, or combinations thereof;
wherein the polymer scaffold is, the releasing material is, or both the polymer scaffold and the releasing material are partially dissolved away where the releasing material encapsulated biomolecules are immobilized, the partial dissolving causing the releasing material encapsulated biomolecules to adhere to the polymer scaffold;
wherein the biomolecules are selected from recombinant human bone morphogenetic protein-2, recombinant human bone morphogenetic protein-7, recombinant human platelet-derived growth factor BB, tumor necrosis factor-alpha, hepatocyte growth factor, interleukin-8, angiogenin, angiopoietin-1, and combinations thereof, and wherein the releasing material is selected from poly (lactic-co-glycolic acid) and poly(L-lactic acid).

2. The porous object as defined in claim 1 wherein the releasing material encapsulated biomolecules are nanoparticles, microparticles, nanospheres, microspheres, or combinations thereof.

3. A method for making the porous object of claim 1, the method comprising:
  encapsulating biomolecules in a releasing matrix, wherein the biomolecules are selected from recombinant human bone morphogenetic protein-2, recombinant human bone morphogenetic protein-7, recombinant human platelet-derived growth factor BB, tumor necrosis factor-alpha, hepatocyte growth factor, interleukin-8, angiogenin, angiopoietin-1, and combinations thereof, and wherein the releasing material is selected from poly (lactic-co-glycolic acid) and poly(L-lactic acid); and
  immobilizing the encapsulated biomolecules on at least one of internal pore surfaces, external pore surfaces, or combinations thereof of a polymer scaffold having nano-fibrous walls, wherein immobilizing involves partially dissolving away the polymer scaffold, the releasing material, or both the polymer scaffold and the releasing material, which causes the releasing material encapsulated biomolecules to adhere to the polymer scaffold.

4. The method as defined in claim 3 wherein immobilizing is accomplished by:
  suspending the releasing material encapsulating the biomolecules in a non-solvent of both the polymer scaffold and the releasing material;
  adding the suspension to the polymer scaffold;
  removing the non-solvent to form the polymer scaffold having the releasing material encapsulating the biomolecules loosely adhered on: at least one of the internal pore surfaces; at least one of the external pore surfaces; or combinations thereof;
  exposing the polymer scaffold and the loosely adhered releasing material encapsulating the biomolecules to a solvent, thereby partially dissolving the polymer scaffold, the releasing material, or both the polymer scaffold and the releasing material and causing the releasing material encapsulating the biomolecules to adhere to the polymer scaffold; and
  removing the solvent, thereby forming the porous material having the releasing material encapsulating the biomolecules immobilized on: at least one of the internal pore surfaces; at least one of the external pore surfaces; or combinations thereof.

5. The method as defined in claim 4 wherein the solvent is selected a mixture of cyclohexane and tetrahydrofuran (THF) present in a volume ratio ranging from about 70:30 to about 95:5; a mixture of hexane and THF present in a volume ratio ranging from about 70:30 to about 95:5, a mixture of cyclohexane and acetone present in a volume ratio ranging from about 80:20 to about 95:5, a mixture of hexane and acetone present in a volume ratio ranging from about 80:20 to about 95:5, a mixture of ethanol and acetone present in a volume ratio from about 80:20 to about 95:5, a mixture of ethanol and THF present in a volume ratio ranging from about 70:30 to about 95:5, a mixture of isopropanol and THF present in a volume ratio ranging from about 70:30 to about 95:5, a mixture of isopropanol and acetone present in a volume ratio ranging from about 80:20 to about 95:5, a mixture of ethanol and chloroform present in a volume ratio ranging from about 90:10 to about 95:5, and a mixture of ethanol and dichloromethane present in a volume ratio ranging from about 90:10 to about 95:5.

6. The method as defined in claim 3 wherein the biomolecules are interleukin-8, angiogenin, angiopoietin-1, and combinations thereof, and wherein encapsulating the biomolecules includes:
  forming a first emulsion including the angiogenic or mitogenic factors and a polymeric material;
  forming a second emulsion including the first emulsion and an aqueous solution; and
  removing fluid from the second emulsion.

7. The method as defined in claim 6 wherein immobilizing is accomplished by:
  suspending the releasing material encapsulating the biomolecules in a non-solvent or poor solvent of both the polymer scaffold and the releasing material;
  adding the suspension to the polymer scaffold;
  removing the non-solvent to form the polymer scaffold having the releasing material encapsulating the biomolecules loosely adhered on a surface of the polymer scaffold;
  exposing the polymer scaffold and the loosely adhered releasing material encapsulating the biomolecules to partial solvent or a solvent/non-solvent mixture, thereby partially dissolving the polymer scaffold, the releasing material, or both the polymer scaffold and the releasing material and causing the releasing material encapsulating the biomolecules to adhere to the polymer scaffold; and
  removing the partial solvent or solvent/non-solvent mixture, thereby forming the p polymer scaffold having the releasing material encapsulating the biomolecules immobilized thereon.

8. The method as defined in claim 3 wherein encapsulating the biomolecules is accomplished by simple emulsion, extrusion, phase separation, self-assembly, spray-drying, complexing, blending, chemical reaction or association, dendrimer techniques, or combinations thereof.

9. A porous object formed by the method of claim 3.

10. A method for controlling release of a biomolecule in vivo, the method comprising:
  encapsulating the biomolecule in a releasing material, wherein the biomolecules are selected from recombinant human bone morphogenetic protein-2, recombinant human bone morphogenetic protein-7, recombinant human platelet-derived growth factor BB, tumor necrosis factor-alpha, hepatocyte growth factor, interleukin-8, angiogenin, angiopoietin-1, and combinations thereof, and wherein the releasing material is selected from poly(lactic-co-glycolic acid) and poly(L-lactic acid); and
  immobilizing a predetermined number of the encapsulated biomolecules on: at least one of internal pore surfaces; at least one of external pore surfaces; or combinations thereof of a polymer scaffold having nano-fibrous walls, wherein immobilizing involves partially dissolving away the polymer scaffold, the releasing material, or both the polymer scaffold and the releasing material, which causes the releasing material encapsulated biomolecules to adhere to the polymer scaffold.

11. The method as defined in claim 10, further comprising implanting the polymer scaffold having the encapsulated biomolecules immobilized thereon in a patient.

12. The method as defined in claim 11, further comprising repairing or regenerating tissue via the implanted polymer scaffold, the tissue selected from hard tissue, soft tissue, and combinations thereof.

13. The method as defined in claim 10, further comprising modulating release kinetics of the polymer scaffold by i) increasing or decreasing an amount of the biomolecule, ii) increasing or decreasing a molecular weight of the releasing material, or iii) combinations of i and ii.

14. The method as defined in claim 10 wherein the polymer scaffold having the encapsulated biomolecules thereon is configured to induce gene expression and tissue neogenesis in vivo.

* * * * *